US008999894B2

(12) United States Patent
Blanchard et al.

(10) Patent No.: US 8,999,894 B2
(45) Date of Patent: Apr. 7, 2015

(54) NUCLEIC ACID-LIKE PROTEINS

(75) Inventors: John S. Blanchard, Pelham, NY (US);
Matthew W. Vetting, Ossining, NY (US); Subray S. Hegde, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1640 days.

(21) Appl. No.: 11/918,109

(22) PCT Filed: Apr. 18, 2006

(86) PCT No.: PCT/US2006/014823
§ 371 (c)(1),
(2), (4) Date: Dec. 5, 2008

(87) PCT Pub. No.: WO2006/113841
PCT Pub. Date: Oct. 26, 2006

(65) Prior Publication Data
US 2009/0131266 A1    May 21, 2009

Related U.S. Application Data

(60) Provisional application No. 60/673,156, filed on Apr. 20, 2005.

(51) Int. Cl.
C40B 30/04 (2006.01)
C07K 14/35 (2006.01)
C07K 14/195 (2006.01)
A61K 38/00 (2006.01)

(52) U.S. Cl.
CPC .................. *C07K 14/35* (2013.01); *C40B 30/04* (2013.01); *A61K 38/00* (2013.01); *C07K 14/195* (2013.01)

(58) Field of Classification Search
None
See application file for complete search history.

(56) References Cited

U.S. PATENT DOCUMENTS

| 6,852,834 B2 | 2/2005 | Chilkoti |
| 7,271,243 B2 * | 9/2007 | Dumas Milne Edwards et al. ............................ 530/350 |
| 2001/0034050 A1 | 10/2001 | Chilkoti |

OTHER PUBLICATIONS

Core et al, Molecular Microbiology, 2003, 49(6), 1509-22.*
Schmidt et al, Biochem. J. 1991, 280, 411-414.*
Tran et al, pNAS, 2002, 99, 8, 5638-42.*
Brinker et al Journal of Biological Chemistry (2002), 277(22), 19265-19275.*
Montero, Antimicrob. Agents Chemother. 45, 3387-3392 (2001).*
International Search Report and the Written Opinion of the International Searching Authority.
International Preliminary Report on Patentability for PCT Application No. PCT/US06/14823, dated Nov. 1, 2007.

* cited by examiner

Primary Examiner — Christian Boesen
(74) Attorney, Agent, or Firm — Amster, Rothstein & Ebenstein LLP

(57) ABSTRACT

Methods are provided for labeling and for detecting DNA-interacting proteins with an assayable label, comprising combining the DNA-interacting protein with a mfpA pentapeptide repeat family protein that has been purified and that binds to the protein, wherein the mfpA pentapeptide repeat family protein is bound to an assayable label.

9 Claims, 9 Drawing Sheets

How Robust is the RHQBH fold?

*Nostoc punctiforme*
Contains 40 predicted PRP's
Smallest is NP0275
98 Amino acids
C-terminal pentapeptide repeat

```
MDVEK  LRQLY  AAGE                14
RDFSI  VDLRG  AVLEN  INLSG         34
AILHG  AMLDE  ANLQQ  ANLSR         54
ADLSG  ATLNG  ADLRG  ANLSK         74
ADLSD  AILDN  AILEG  AILDE         94
AVLN                               98
```

Structure Solved using C-terminal Coils 5-8 of MfpA

The Structure of NP0275: the Second PRP 2.7 Angstrom Model and Electron Density

FIG. 6

| Genomic Environment of Np 0275 | | | |
|---|---|---|---|
| MDVEK | LRQLY | AAGE | |
| RDFSI | VDLRG | AVLEN | INLSG | 14
| AILHG | AMLDE | ANLQQ | ANLSR | 34
| ADLSG | ATLNG | ADLRG | ANLSK | 54
| ADLSD | AILDN | AILEG | AILDE | 74
| AVLNX | ANLKA | ANLEQ | AILSH | 94
| ANIRE | ADLSE | ANLEA | ADLSG | 98
| ADLAI | ADLSE | ANLHQ | AALER | |
| ANLTG | ANLED | ANLEG | TILEG | |
| GNNNL | AT | | |

Np0275 (98 AA)

Np0276 (75 AA)

Np0275/6 (181 AA)

All Leucine hydrophobic Core

Stop Codon (X) Converted to E, "full-length" protein expressed Structure Solved using the 98 AA Np0275 Structure Np0275/6 Has A Nearly Continuous Cavity in the Interior Cut-Away Top View (Coils 1-3)

Cut-Away Side View

NUCLEIC ACID-LIKE PROTEINS

CROSS-REFERENCE TO RELATED APPLICATION

This application claims the benefit of U.S. Provisional Patent Application Ser. No. 60/673,156, filed Apr. 20, 2005.

STATEMENT REGARDING FEDERALLY SPONSORED RESEARCH OR DEVELOPMENT

This invention was made with government support under Grant Nos. AI33696, AI60899 and T32 AI07501 awarded by The National Institutes of Health. The government has certain rights in the invention.

BACKGROUND OF THE INVENTION (1) Field of the Invention

The present invention generally relates to structures or proteins and manipulations thereto. More specifically, the invention relates to proteins that imitate DNA and are able to bind to DNA-interacting macromolecules and affect the macromolecules' action.

(2) Description of the Related Art

REFERENCES CITED

Ali, J. A., Jackson, A. P., Howells, A. J., and Maxwell, A. *Biochemistry* 32: 2717-2724 (1993).
Aubry A., X.-S. Pan, L. M. Fisher, V. Jarlier, E. Cambau, *Antinzicrob. Agents Chemother.* 45, 1281-1288 (2004).
Bateman A., A. G. Murzin, S. A. Teichman, *Protein Sci* 7, 1477-1480 (1998).
Bateman A. et al., *Nucleic Acid Res.* 32, D138-141 (2004).
Bateman, A., Murzin, A. G. and Teichman, S. A. *Prot. Sci.* 7, 1477-1480 (1998).
Black K., W. J. Buikema, R. Haselkorn, *J. Bact.* 177, 6440-6448 (1995).
Brunger, A. T., Adams, P. D., et al. *Acta Cryst. sec. D.* 54, 905-921 (1998).
Cambau E., W. Sougakoff, M. Besson, C. Truffot-Pernot, J. Grosset, V. Jarlier, *J. Infect. Dis.* 170, 479-483 (1994).
Cole S. T. et al., *Nature* 393, 537-544 (1998).
Cowtan K., Joint CCP4 and ESF-EACBM Newsletter on Protein Crystallography, 31, 34-38 (1994).
Crofton J. et al., Health Organization, Geneva, Switzerland (1997).
Daigle, D. M., McKay, G. A., Thompson, P. R. and Wright, G. D. *Chemistry & Biology* 6, 11-18 (1999).
Drlica K., M. Malik, *Curr. Top. Med. Chem.* 3, 249-282 (2003).
Emsley, P., Charles, I. G., Fairweather, N. F. and Isaacs, N. *Nature* 381, 90-92 (1996).
Emsley, P. and K. Cowtan, Coot: model-building tools for molecular graphics. *Acta Crystallogr D Biol Crystallogr* 60(Pt 12 Pt 1): p. 2126-32 (2004).
Gamido M. C., M. Herrero, R. Kolter, F. Moreno, *EMBO J.* 7, 1853-1862 (1988).
Ginsburg A. S. et al., *N. Engl. J. Med.* 349, 1977-1978 (2003).
Guillemin I., V. Jarlier, E. Cambau, *Antimicrob. Agents Chemother.* 42, 2084-2088 (1998).
Hata M. et al., (2005) *Antimicrob. Agents Chemother.* 49, 801-803.
Heddle J. G. et al., *J. Mol. Biol.* 307, 1223-1234 (2001).
Hegde, S. S., et al., A fluoroquinolone resistance protein from *Mycobacterium tuberculosis* that mimics DNA. *Science* 308(5727): p. 1480-3 (2005).
Ichetovkin, I. E., Abramochkin, G. and Shrader, T. E., *J Biol. Chem.* 272: 33009-33014 (1997).
Izuta S. et al., *J. Biochem.* (Tokyo) 112, 81-87 (1992).
Jacoby G. A., N. Chow, K. B. Waites, *Antimicrob. Agents Chemother.* 47, 559-562 (2003).
Ji B., N. Lounis, C. Truffot-Pemot, P. Bonnafous, J. Grosset, *Antinicrob. Agents Chemother.* 42, 2066-2069 (1998).
Jonas D. et al., *Antimicrob. Agents Chemother.* 49, 773-775 (2005).
Jones, T. A., *J. Applied Cryst.* 11, 268-272 (1978).
Kamei, A., Yoshihara, S., Yuasa, T., Geng, X. and Ikeuchi, M. *Current Microbiol.* 46, 296-301 (2003).
Kieber-Emmons et al., *Curr. Opin. Biotechnol.* 8, 435-441 (1997).
Kobe, B. *Nat. Struct. Biol.* 3, 977-980 (1996).
Krogh, A., Brown, M., Mian, I. S., Sjolander, K. and Haussler, D. *J. Mol. Biol.* 235, 1501-1531 (1994).
Leslie, A. G., The integration of macromolecular diffraction data. *Acta Crystallogr D Biol Crystallogr* 62(Pt 1): p. 48-57 (2006).
Liu D., D et al., *Cell* 94, 573-583 (1998).
Mizuuchi, K., Mizuuchi, M., O'Dea, M. H., and Gellert, M. (1984) *J. Biol. Chem.* 259, 9199-9201.
Montero C., G. Mateu, R. Rodriguez, H. E. Takiff, *Antimicrob. Agents Chemother.* 45, 3387-3392 (2001).
Morais Cabral J. H. et al., *Nature* 388, 903-906 (1997).
Morita M. et al., *Biosci. Biotechnol. Biochem.* 63, 563-566 (1999).
Murshudov, G. N., A. A. Vagin, and E. J. Dodson, Refinement of macromolecular structures by the maximum-likelihood method. *Acta Crystallogr D Biol Crystallogr* 53(Pt 3): p. 240-55 (1997).
Nakanishi A., S. Imajoh-Ohmi, F. Hanaoka, *J. Biol. Chem.* 277, 8949-8954 (2002).
Navaza, J., An automated package for molecular replacement. *Acta Cryst* A50: p. 157-163 (1994).
Navaza, J., *Acta Cryst. D.* 57, 1367-1372 (2001).
Nichols, A., Bharadwaj, R., et al., *Biophys. J.* 64, A166 (1993).
Nuermberger E. L. et al., *Am. J. Respir. Crit. Care Med.* 170, 1131-1134 (2004).
Otwinski, Z., Proceedings of the CCP4 Study Weekend, Warrington, Daresbury Laboratory (1993).
Parsons L. M., D. C. Yeh, J. Orban, *Proteins; Struct., Funct, and Bioinform.* 54, 375-383 (2004).
Perrakis, A., wARP: Improvement and Extension of Crystallographic Phases by Weighted Averaging of Multiple-Refined Dummy Atomic Models. *Acta Cryst.* D53(Pt 4): p. 448-55 (1997).
Pierrat O. A., A. Maxwell, *J. Biol. Chem.* 278, 35016-15023 (2003).
Poole K., *Antimicrob. Agents Chemother.* 44, 2233-2241 (2000).
Raetz, C. R. H. and Roderick, S. L. *Science* 270, 997-1000 (1995).
Reece, R. J., and Maxwell, A. *J. Biol. Chem.* 264, 19648-19653 (1989).
Ripka et al., *Curr. Opin. Chem. Biol.* 2, 441-452 (1998).
Romanowski M. J., S. A. Gibney, S. K. Burley, *Proteins: Struct. Func. Genetics* 47, 403-407 (2002).
Sanderson, *Med. Res. Rev.* 19, 179-197 (1999).
Sullivan E. A. et al., *Lancet* 345, 1148-1150 (1995).
Takiff, H. E et al., *Antimicrob. Agents Chemother.* 38, 773-780 (1994).

Terwilliger, T. C., *Acta Cryst. sec. D.* 58, 1937-1940 (2002).
Tran J. H., G. A. Jacoby, D. C. Hooper, *Antimicrob. Agents Chemother.* 49, 118-125 (2005).
Tran J. H., G. A. Jacoby, *Proc. Nat'l Acad. Sci. USA* 99, 5638-5642 (2002).
Vagin, A. and A. Teplyakov, An approach to multi-copy search in molecular replacement. *Acta Crystallogr D Biol Crystallogr.* 56 Pt 12: p. 1622-4 (2000).
Vetting, M. W., Magnet, S., Nieves, E., Roderick, S. L. and Blanchard, J. S. *Chemistry & Biology* 11, 565-573 (2004).
Vetting, M. W. et al. *Biochemistry* 45, 1-10 (2006).
Walkinshaw M. D. et al., *Mol. Cell.* 9, 187-194 (2002).
Wilmot C. J. R., A. Maxwell, *Antimicrob. Agents Chemother.* 37, 126-127 (1993).
Xu C., B. N. Kreiswith, S. Sreevatsan, J. M., Musser, K. Drlica, *J. Infect. Dis.* 174, 1127-1130 (1996).
Yoder, M. D., Keen, N. T. and Jurnak, F. *Science* 260, 1503-1507 (1993).

Pentapeptide Repeat Family Proteins

The first protein identified with what is now recognized as the pentapeptide repeat motif was the hglK-encoded protein from Anabena sp. Strain PCC 7120 (Black et al., 2005). This filamentous cyanobacterium forms heterocysts, specialized cells capable of fixing nitrogen when reduced forms of nitrogen are unavailable. Chemical mutagenesis of the PCC 7120 strain identified mutants that were incapable of forming the thick glycolipid outer cell component characteristic of heterocysts. Complementation analysis revealed that the hglK gene could reverse the mutant phenotype and that, in the mutant strain, a mutation had introduced a stop codon at amino acid position 496 of the 727 amino acid protein. Starting at position 501, a series of 36 uninterrupted, tandem repeats of a pentapeptide with the consensus sequence, ADLSG (SEQ ID NO:6), were observed. The amino terminus contained four possible membrane spanning domains, suggesting that these might anchor the protein into the membrane, and that glycolipid transport or assembly into the heterocyst might be the function of the pentapeptide repeat.

The first bioinformatic approach to the genome-wide identification of pentapeptide repeat proteins was reported in 1998 by Bateman et al. (1998), who searched the *Synechocystis* sp. PCC 6803 genome using a single sequence (SLR1819). This putative 331 amino acid protein contained 61 pentapeptide repeats representing 91% of the total sequence. After a 14 residue N-terminal sequence, 25 tandem pentapeptide repeats follow, that are then interrupted by a 6 amino acid sequence that does not correspond to the consensus repeat, followed by 32 uninterrupted repeats and a short 6 amino acid C-terminal sequence. Using this query sequence and the Blast program, 15 additional *Synechocystis* sp. PCC 6803 proteins that contained between 13 and 44 tandem pentapeptide repeats were identified. Several additional sequences were identified as being members of the pentapeptide repeat family, including the McbG gene product, known to confer resistance to the antibacterial Microcin B17 (Garrido et al., 1988). In this work, they also proposed a structural model, in which each of the central Leu or Phe side chains was packed in the interior of a right-handed β-helix, in a fold highly reminiscent of the left-handed β-helix structurally characterized for hexapeptide repeat proteins (Yoder et al., 1993; Raetz and Roderick, 1995; Emsley et al., 1996; Kobe 1996).

A more robust approach to the identification of proteins that contain pentapeptide repeat motifs has used Hidden Markov Models (HMM's; Krogh et al., 1994) containing eight consecutive pentapeptide repeats. Both the COG and Pfam databases have identified pentapeptide repeat proteins that in both cases are termed "uncharacterized low complexity proteins". COG1357 lists 105 pentapeptide repeat proteins from 27 species, while the Pfam database (www.sanger.ac.uk/cgi-bin/Pfam) currently lists 1020 pentapeptide repeat-containing proteins. These include all members identified by Bateman et al. (1998), as well as all proteins listed in the COG1357 family. While the vast majority of these are found in prokaryotes, there are examples of proteins containing pentapeptide repeat domains in *Plasmodium falciparum, Anopheles gambia, Arabidopsis*, zebrafish, mouse and human. With the exception of the *Plasmodium falciparuin* PRP, all higher eukaryotic PRP's contain 32 uninterrupted tandem pentapeptide repeats at the C-terminus of 300-390 residue proteins whose N-terminus is a cytoplasmic tetramerization domain of voltage-gated $K^+$ channels. PRP's have also been identified in bacteriophages (st104 and st64t) as well as mycobacteriophages.

While many bacteria contain one or few PRP's (see below, *Mycobacterium tuberculosis*), some microorganisms, especially the photosynthetic cyanobacteria and *Anabena*, have numerous chromosomally-encoded PRP's. *Synechocystis* sp. strain 6803 has 16 PRP's. We have generated a HMM from the *M. tuberculosis* MfpA protein containing 12 repeats of the pentapeptide and can identify 40 PRP's in *Nostoc punctiforme* which range in size from 98 amino acids to >400 residues. As noted above in the case of the *Anabena* HglK protein and the human voltage-gated potassium channel tetramerization protein, PRP's often contain multiple domains with the PRP domain usually occurring at the C-terminus of these poly-domain proteins.

The majority of PRP's are polydomain proteins with additional domains, some of which are homologous to catalytic domains. The best studied is the *Synechocystis* sp. Strain 6803 SpkB protein. This protein has an N-terminal domain than is homologous to mammalian protein Ser/Thr kinase domains, and a C-terminal pentapeptide repeat domain (Kamei et al., 2003). The SpkB protein is one of thirteen protein encoded in the genome of this organism with putative Ser/Thr protein kinase activity, but the only one that contains an additional pentapeptide repeat domain. The SpkB protein both catalyzes it's own autophosphorylation, as well as the phosphorylation of bovine myelin basic protein and casein as well as calf thymus histones. The ability of this bacterial protein to phosphorylate mammalian proteins is highly reminiscent of bacterial aminoglycoside phosphotransferases that have been shown to phosphorylate both aminoglycoside antibiotics, conferring high-level resistance to these compounds, as well as mammalian proteins (Daigle et al., 1999). A second example of a polydomain PRP with an N-terminal catalytic domain is the *Bacillus* ant/racis PRP: In this case, the protein has an N-terminal Gcn5-related N-acetyltransferase (GNAT) domain similar to those found in eukaryotic histone acetyltransferases. Although this protein has not been functionally characterized to date, it is again highly reminiscent of other bacterial aminoglycoside N-acetyltransferases that acetylates mammalian histone proteins (Vetting et al., 2004).

It would be desirable to further understand the structure and functions of pentapeptide repeat family proteins. The present invention addresses that need.

SUMMARY OF THE INVENTION

Accordingly, the inventors have discovered that pentapeptide repeat family proteins are capable of mimicking nucleic acids to the extent that they can bind to nucleic acid-binding macromolecules such as proteins.

Thus, in some embodiments, the invention is directed to recombinant pentapeptide repeat family proteins comprising at least one mutation of an $i^{-1}$, $i^{+1}$, and/or $i^{+2}$ amino acid residue.

In other embodiments, the invention is directed to vectors comprising a nucleic acid sequence encoding the above-described pentapeptide repeat family proteins.

The invention is also directed to protein libraries comprising at least two of the above pentapeptide repeat family proteins, where the at least two proteins comprise different amino acid sequences.

In further embodiments, the invention is directed to vector libraries comprising at least two of the above-described vectors, where the at least two vectors encode pentapeptide repeat family proteins having different amino acid sequences from each other.

Additionally, the invention is directed to methods of identifying a pentapeptide repeat family protein with an assayable phenotype. The methods comprise
  (a) creating the above-described vector library;
  (b) transfecting cells with the library from (a); and
  (c) assaying the cells for the phenotype, where cells having the phenotype comprise a vector encoding a pentapeptide repeat family protein responsible for the phenotype.

The invention is further directed to methods of labeling a nucleic acid-interacting macromolecule. The methods comprise combining the nucleic acid-binding macromolecule with a pentapeptide repeat family protein that binds to the macromolecule. In these embodiments, the pentapeptide repeat family protein further comprises an assayable label.

In additional embodiments, the invention is directed to methods of detecting a nucleic acid-interacting macromolecule. The methods comprise combining the nucleic acid-binding macromolecule with a pentapeptide repeat family protein that binds to the macromolecule, then detecting the pentapeptide repeat family protein that is bound to the nucleic acid-interacting macromolecule.

BRIEF DESCRIPTION OF THE DRAWINGS

FIG. 6 shows the genomic environment of NP0275, including the pentapeptide repeat of NP0276 (SEQ ID NO:3).

DETAILED DESCRIPTION OF THE INVENTION

The present invention is partly based on the discovery that pentapeptide repeat family proteins are capable of mimicking nucleic acids to the extent that they can bind to nucleic acid-binding macromolecules such as proteins. See Example. Mutants of pentapeptide repeat family proteins are useful as novel proteins that bind nucleic acid-binding macromolecules.

Thus, in some embodiments, the invention is directed to recombinant pentapeptide repeat family proteins comprising at least one mutation of an $i^{-1}$, $i^{+1}$, and/or $i^{+2}$ amino acid residue.

As used herein, a "pentapeptide repeat family protein" or "PRP" is a member of Pfam:PF:00805 (see Pfam database at www.sanger.ac.uk/cgi-bin/Pfam). It is noted that, although the PF:00805 description in the Pfam database describes the pentapeptide repeat as approximately A(D/N)LXX, where X is any amino acid, there is a great deal of variation in these repeats (see FIG. 2D). Thus, a broader but more accurate description of the characteristic pentapeptide repeat is (Hy/Po)X(Hy)XX, where Hy is a hydrophobic residue, Po is an uncharged polar residue, and X is any amino acid.

As used herein, $i^{-1}$, $i^{+1}$, and/or $i^{+2}$ are amino acid residues immediately before, immediately after, and the second after, respectively, a third amino acid residue (i.e., the central residue) in a pentapeptide repeat in the protein. This central residue is also denoted "i".

The mutant pentapeptide repeat family proteins of the present invention can exist as monomers, dimers, or at any higher multimer level. The oligomerization state can be determined by any of several known methods. The most straightforward methods involve determining the apparent molecular weight of the multimer complex and from this determining the number of associated monomer components (this can be accomplished by dividing this apparent molecular weight by the molecular weight of the monomer). Analytical ultracentrifugation is a particularly suitable technique for this purpose. The specifics of this method are known to those skilled in the art. See, e.g., P. Graceffa et al., J. Biol. Chem. 263, 14196-14202 (1988), and can be summarized as follows. The material of interest is placed in a sample cell and spun very rapidly in a model E ultracentrifuge equipped with the appropriate detection devices. Information collected during the experiment combined with the amino acid composition of the peptide allows for the determination of the apparent MW of the multimer complex. Fast Protein Liquid Chromatography (FPLC) can also be used for this purpose. This technique is different from the above in that, as a type of chromatography, it ultimately requires reference back to some primary standard (determined by analytical ultracentrifugation). These determinations are carried out under non-denaturing (native) conditions and when referenced to the appropriate standards can be used to identify peptide and protein oligomerization states.

Figure 3:
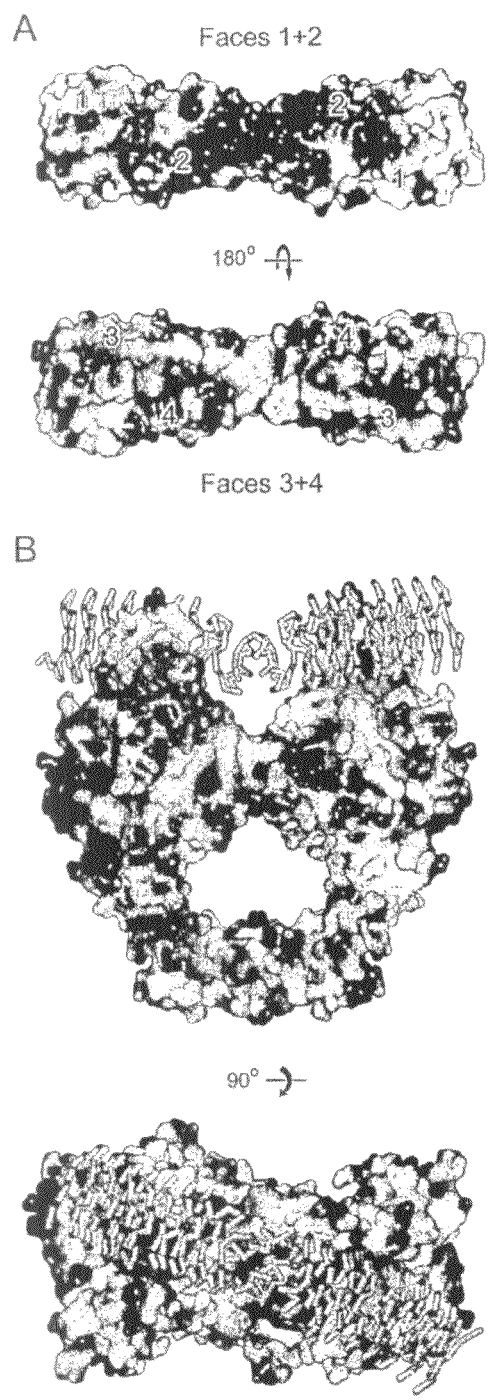
FIG. 3 shows the electrostatics of MfpA/GyrA and a Model of Their Interaction. Panel A is a surface representation of the MfpA dimer showing either faces 1 and 2 (front) or faces 3 and 4 (back). Panel B shows the molecular model of dimeric MfpA bound to dimeric GyrA59 (surface) in two orthogonal orientations.

Since pentapeptide repeat family proteins imitate nucleic acids partly due to its significant negative electrostatic surface potential on the faces of the protein that interact with nucleic acid-interacting macromolecules, it is preferred that the mutations in the protein is on a face of the protein having a negative electrostatic surface potential. Examples of such faces are face 1 and face 2 as shown in FIG. 3. Thus, in some embodiments, the mutation is preferably on face 1 or face 2 as shown in FIG. 3. This includes proteins where the faces analogous to face 1 or face 2 can be discerned, even if not having an identical amino acid sequence on those faces as of Mfp1A, shown in FIG. 3. In other cases, however, the nucleic acid-interacting macromolecule would be expected to interact with all four faces. Such a nucleic acid-interacting macromolecule is a DNA polymerase or other enzymes.

In these embodiments, the pentapeptide repeat family protein mutation is an amino acid addition, deletion, or preferably a change from the naturally occurring amino acid at the same position in the protein from which the mutant was derived.

These mutants can be made by any known method, for example by chemical synthesis methods, or preferably by mutating the gene for the protein and then expressing the mutated gene. The genes can be mutated by directed (e.g., cassette mutagenesis, site-directed mutagenesis, PCR mutagenesis, etc.) or random (e.g., chemical or ionizing radiation mutagenesis, methods using error-prone DNA polymerases, etc.) mutagenesis methods.

The invention is not limited to any particular mutations of an $i^{-1}$, $i^{+1}$, and/or $i^{+2}$ amino acid residue, although in many embodiments, nonconservative substitutions are preferred, since those substitutions would be expected to modify the binding characteristics of the pentapeptide repeat family protein more than conservative substitutions. However, conservative substitutions are useful when only small changes in binding characteristics of the pentapeptide repeat family protein are desired.

As used herein, a "conservative substitution" connotes an individual substitution to an amino acid sequence that alters a single amino acid, where the substitute amino acid has a similar polarity and charge. Conservatively modified variants typically provide similar biological activity as the unmodified polypeptide sequence from which they are derived. For example, substrate specificity, enzyme activity, or ligand/receptor binding is expected to be at least 30%, 40%, 50%, 60%, 70%, 80%, or 90% of the native protein for its native substrate. The following six groups each contain amino acids that are conservative substitutions for one another:
1) Serine (S), Threonine (T), Glycine (G), Cysteine (C);
2) Aspartic acid (D), Glutamic acid (E);
3) Asparagine (N), Glutamine (Q);
4) Arginine (R), Lysine (K), Histidine (H);
5) Alanine (A), Isoleucine (I), Leucine (L), Methionine (M), Valine (V); and
6) Phenylalanine (F), Tyrosine (Y), Tryptophan (W).

An example of a useful mutation in these embodiments is the addition or subtraction of a proline residue to the protein (see Example). As discussed in the Example below, a proline residue introduces a tilt in the helical axis of the protein. Preferably, the proline residue is or was at an $i^{+2}$ position.

Another example of a useful mutation is one that changes an amino acid residue to a charged amino acid residue. Preferably, the residue is changed to have a negative charge, since this would tend to make the protein more nucleic acid-like. Other conservative and nonconservative mutations, additions or deletions are envisioned as within the scope of the invention.

The pentapeptide repeat family proteins of these embodiments can also incorporate amino acid peptidomimetics as substitutes for one or more than one amino acid moiety. As used herein, an amino acid mimetic or peptidomimetic is a compound that is capable of mimicking a natural parent amino acid in a protein, in that the peptidomimetic does not affect the activity of the protein. Proteins comprising peptidomimetics are generally not substrates of proteases and are likely to be active in vivo for a longer period of time as compared to the natural proteins. In addition, they could be less antigenic and show an overall higher bioavailability. The skilled artisan would understand that design and synthesis of peptidomimetics that could substitute for any particular oligopeptide (such as the inhibitors of this invention) would not require undue experimentation. See, e.g., Ripka et al., 1998; Kieber-Emmons et al., 1997; Sanderson, 1999.

The proteins of these embodiments can also comprise amino acid deletions or additions from the wild-type pentapeptide repeat family protein. Included here are proteins where one to several amino acids or larger portions, e.g., protein domains or portions thereof. Naturally occurring pentapeptide repeat family proteins generally include non-pentapeptide repeat domains that may affect the protein's functions. Examples include transmembrane domains, signal peptides, kinase domains, N-acetyltransferase domains, and voltage-gated $K^+$ channel domains. See Pfam database. One to several of those domains, or one to several pentapeptide repeats can be deleted, and any known domain may be added. This may change functional characteristics of the protein, e.g., its binding and/or effector characteristics Other additions to the protein that are within the scope of the invention are additions of: antigen epitopes that are not a natural pentapeptide repeat family protein antigens; protease target sites; other nucleic acid binding regions; and regions facilitating purification or detection (e.g., fluorescent protein, oligohistidine moiety, etc.). Methods for producing such changes are well known and routine and preferably involve manipulation of the protein by recombinant DNA methods.

These mutant proteins can be derived from any pentapeptide repeat family protein now known or later discovered. Examples include MfpA, MtMfpA, McbG, Qnr, the 98 amino acid *Nostoc punctiforme* gene7305, the 330 amino acid *Nostoc punctiforme* gene 881 that contains two interruptions in an otherwise uninterrupted series of 64 tandem pentapeptide repeats, the 505 amino acid *Nostoc punctiforme* gene 71 that is predicted to encode an N-terminal protein Ser/Thr kinase domain and a C-terminal pentapeptide repeat domain containing 28 uninterrupted pentapeptide repeats and the *Bacillus anthracis* PRP that contains an N-terminal histone acetyltransferase domain and an N-terminal pentapeptide repeat domain. Preferred pentapeptide repeat family proteins that are mutated to form the invention mutants are MfpA, MtMfpA, McbG, and Qnr, since those are the most studied PRPs. Most preferably, the protein is a mutant of MfpA.

In preferred embodiments, the proteins of these embodiments bind to a nucleic acid-interacting macromolecule, preferably a DNA-interacting protein. These DNA-interacting proteins are preferably naturally occurring. The naturally occurring proteins can be from any organism, including prokaryotes or archaea, including pathogenic bacteria. They proteins could also be naturally occurring in eukaryotes such as mammalian parasites, or mammals, including rodents and humans. The DNA-interacting protein can also be from a virus.

In some embodiments, the DNA-interacting protein is a DNA metabolizing or DNA catabolizing enzyme, including but not limited to DNA gyrases, DNA polymerases, RNA polymerases, reverse transcriptases, DNA ligases, RNA ligases, polynucleotide kinases, alkaline phosphatases, pyrophosphatases, DNA glycosylases, topoisomerases, nicking enzymes, restriction endonucleases, ribonucleases, recombinases, deoxyribonucleases, and exonucleases. In some preferred embodiments, the DNA catabolizing enzyme is a DNA gyrase.

In other embodiments, the DNA-interacting protein is a DNA-binding protein, including but not limited to single stranded DNA binding proteins, transcription factors, repressors, activators, enhancers, helix-turn-helix proteins, zinc finger proteins, leucine zipper proteins, helix-loop-helix proteins, steroid receptors, and homeodomain proteins.

Preferably, the mutant protein of these embodiments binds to the nucleic acid-interacting macromolecule with a different affinity, avidity or specificity than the naturally-occurring pentapeptide repeat family protein from which the mutant was derived.

The pentapeptide repeat family protein of these embodiments can also further comprise an assayable label, which is useful for, e.g., assaying for a nucleic acid-interacting molecule that binds to the pentapeptide repeat family protein. These embodiments are not limited to any particular type of assayable label, and includes fluorescent protein domains, oligohistidine sequences, and antigens that are not a natural pentapeptide repeat family protein antigen (e.g., digoxigenin), as discussed above. These embodiments also include fluorescent other visible labels such as fluorescent organic compounds less than 2000 molecular weight or a radioactive molecules.

The invention is also directed to vectors comprising a nucleic acid sequence encoding any of the above-described pentapeptide repeat family proteins comprising at least one mutation of an $i^{-1}$, $i^{+1}$, and/or $i^{+2}$ amino acid residue. In some preferred embodiments, the vector comprises genetic elements allowing transfection of a bacterium with the vector and expression of the protein in the bacterium. In other preferred embodiments, the vector comprises genetic elements allowing transfection of a eukaryotic cell, e.g., a mammalian cell, with the vector and expression of the protein in the cell. These eukaryotic cells can be part of a living multicellular organism.

The vectors of these embodiments can further comprise a promoter operably linked to the nucleic acid sequence encoding the pentapeptide repeat family protein. In these embodiments, the promoter can direct constitutive or inducible expression of the protein in a cell transfected with the vector.

The above-described mutant pentapeptide repeat family proteins are usefully part of a protein library comprising other such mutants, e.g., for screening the mutants for altered binding to nucleic acid-interacting macromolecules. Thus, the present invention is also directed to protein libraries comprising at least two of the pentapeptide repeat family proteins described above comprising at least one mutation of an $i^{-1}$, $i^{+1}$, and/or $i^{+2}$ amino acid residue. In these embodiments, the at least two proteins comprise different amino acid sequences, preferably at least at an $i^{-1}$, $i^{+1}$, and/or $i^{+2}$ amino acid residue. In the most preferred embodiments, the two proteins differ at an amino acid residue on a face of the protein having a negative electrostatic surface potential.

These protein libraries may be in the form of cells comprising the above-described vectors encoding the mutant pentapeptide repeat family proteins, where the mutant proteins are expressed in the cell. Such a library can be particularly useful when the protein is evaluated for changing a phenotype of the cell as a result of an alteration in the nucleic acid-interacting macromolecule binding characteristics due to the mutation.

In related embodiments, the invention is directed to vector libraries comprising at least two of the vectors described above that comprise a nucleic acid sequence encoding a pentapeptide repeat family protein comprising at least one mutation of an $i^{-1}$, $i^{+1}$, and/or $i^{+2}$ amino acid residue. In these embodiments, the at least two vectors encode pentapeptide repeat family proteins having different amino acid sequences from each other. Preferably, the at least two proteins differ at an $i^{-1}$, $i^{+1}$, and/or $i^{+2}$ amino acid residue. In other preferred embodiments, the at least two proteins differ at an amino acid residue on a face of the protein having a negative electrostatic surface potential.

The present invention is also directed to methods of identifying a pentapeptide repeat family protein with an assayable phenotype. The methods comprise (a) creating the above-described vector library comprising at least two of the vectors comprising a nucleic acid sequence encoding a recombinant pentapeptide repeat family protein comprising at least one mutation of an $i^{-1}$, $i^{+1}$, and/or $i^{+2}$ amino acid residue, where the at least two vectors encode pentapeptide repeat family proteins having different amino acid sequences from each other;

(b) transfecting cells with the library from (a); and (c) assaying the cells for the phenotype, wherein cells having the phenotype comprise a vector encoding a pentapeptide repeat family protein responsible for the phenotype. In preferred embodiments, the phenotype is assayable visibly, such as cell death or a change in the growth or other characteristics of the cells. However, the phenotype may also be measured, e.g. by directly measuring changes in activity of a nucleic acid-interacting macromolecule.

Preferably, the phenotype is due to a change in an effect caused by a nucleic acid-interacting macromolecule, such as a DNA-interacting protein, e.g., a DNA metabolizing or DNA catabolizing enzyme such as a DNA gyrase, a DNA polymerase, an RNA polymerase, a reverse transcriptase, a DNA ligase, an RNA ligase, a polynucleotide kinase, an alkaline phosphatase, a pyrophosphatase, a DNA glycosylase, a topoisomerase, a nicking enzyme, a restriction endonuclease, a ribonuclease, a recombinase, a deoxyribonuclease, or an exonuclease (most preferably a DNA gyrase). Other nucleic acid interacting molecules that could be responsible for the assayable phenotype are DNA-binding proteins such as single stranded DNA binding proteins, transcription factors, repressors, activators, enhancers, helix-turn-helix proteins, zinc finger proteins, leucine zipper proteins, helix-loop-helix proteins, steroid receptors, or homeodomain proteins.

In further embodiments, the invention is directed to methods of labeling a nucleic acid-interacting macromolecule. The methods comprise combining the nucleic acid-binding macromolecule with a pentapeptide repeat family protein that binds to the macromolecule, where the pentapeptide repeat family protein further comprises an assayable label. The pentapeptide repeat family protein can be a naturally occurring, or, alternatively, can be a mutant, such as a mutant comprising at least one mutation of an $i^{-1}$, $i^{+1}$, and/or $i^{+2}$ amino acid residue, as described above. In preferred embodiments, the assayable label is a visible label, for example a fluorescent protein, a fluorescent organic compound less than 2000 molecular weight, a radioactive molecule, an antigen that is not a natural pentapeptide repeat family protein antigen, or an oligohistidine sequence.

In related embodiments, the invention is also directed to methods of detecting a nucleic acid-interacting macromolecule. In these embodiments, the methods comprise combining the nucleic acid-binding macromolecule with a pentapeptide repeat family protein that binds to the macromolecule, then detecting the pentapeptide repeat family protein that is bound to the nucleic acid-interacting macromolecule.

The pentapeptide repeat family protein of these embodiments can be unlabeled. In that case, the protein can be detected, e.g., using antibodies that bind specifically to the protein, by known methods. In preferred embodiments, however, the pentapeptide repeat family protein further comprises an assayable label. Examples include visible labels such as fluorescent proteins, or fluorescent organic compounds less than 2000 molecular weight. Other assayable labels are radioactive molecules, antigens that are not a natural pentapeptide repeat family protein antigens, and oligohistidine sequence.

Preferably, the nucleic acid-interacting macromolecule of these embodiments is a DNA-interacting protein, e.g., a DNA metabolizing or DNA catabolizing enzyme such as a DNA gyrase, a DNA polymerase, an RNA polymerase, a reverse transcriptase, a DNA ligase, an RNA ligase, a polynucleotide kinase, an alkaline phosphatase, a pyrophosphatase, a DNA glycosylase, a topoisomerase, a nicking enzyme, a restriction endonuclease, a ribonuclease, a recombinase, a deoxyribonuclease, or an exonuclease. The DNA-interacting protein can also be a DNA-binding protein such as a transcription factor, a repressor, an activator, an enhancer, a helix-turn-helix protein, a zinc finger protein, a leucine zipper protein, a helix-loop-helix protein, a steroid receptor, or a homeodomain protein.

Preferred embodiments of the invention are described in the following Example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the Example.

Example 1

A Fluoroquinolone Resistance Protein from *Mycobacterium tuberculosis* that Mimics DNA Example Summary Fluoroquinolones are gaining increasing significance in the treatment of tuberculosis. Expression of a member of the structurally uncharacterized pentapeptide repeat family of proteins from *Mycobacterium tuberculosis*, MfpA, causes resistance to ciprofloxacin and sparfloxacin. This protein binds to DNA gyrase and inhibits its activity. The three-dimensional structure reveals a previously unreported fold that we have named the right-handed quadrilateral □-helix. MfpA exhibits size, shape and electrostatic similarity to B-form DNA. This represents an unprecedented form of DNA mimicry, and explains both the inhibitory effect on DNA gyrase and fluoroquinolone resistance resulting from the protein's expression in vivo.

Introduction

Fluoroquinolones are synthetic derivatives of nalidixic acid that exert their powerful anti-bacterial activity by interacting with DNA gyrase and DNA topoisomerase IV (Drlica and Malik, 2003). They bind reversibly to the enzyme-DNA complex and stabilize the covalent enzyme tyrosyl-DNA phosphate ester. Fluoroquinolone binding ultimately results in the hydrolysis of the phenolic-phosphomonoester linkage and the accumulation of double-stranded DNA fragments, which is the bactericidal consequence of drug treatment. Structural optimization of fluoroquinolones has led to numerous compounds with substantially improved therapeutic ratios and spectra of activity against Gram-negative and Gram-positive bacterial pathogens.

Fluoroquinolones have received recent interest in the treatment of tuberculosis for several reasons. Resistance to the two bactericidal compounds that act on rapidly growing *Mycobacterium tuberculosis*, isoniazid and rifampicin, has been increasing rapidly, resulting in increased therapeutic failure. Newer third generation fluoroquinolones, including the C8-methoxy-substituted moxifloxacin and gatifloxacin, exhibit powerful in vitro activity against mycobacteria (Crofton et al., 1997; Ji et al., 1998), and can reduce multi-drug treatment regimens from six to four months when substituted for isoniazid (Nuermberger et al., 2004). Resistance to fluoroquinolones remains rare in clinical isolates of *M. tuberculosis* (Sullivan et al., 1995), but can occur rapidly (Ginsburg et al., 2003). Fluoroquinolone resistance has been increasing as its use in the treatment of multi-drug resistant *M. tuberculosis* infections increases (Xu et al., 1996).

High-level resistance to fluoroquinolones has been documented in laboratory strains of mycobacteria, including *M. tuberculosis* and the fast-growing *M. smegmatis* (Takiff et al., 1994; Cambau et al., 1994). Resistance to fluoroquinolones results from single amino acid substitutions in the "fluoroquinolone binding site" of the *M. tuberculosis* gyrA-encoded A subunit of DNA gyrase (Takiff et al., 1994; Cambau et al., 1994). This is the only type II topoisomerase encoded in the *M. tuberculosis* genome (Cole et al., 1998), and thus is the unique target for fluoroquinolones in this organism (Aubry et al., 2004; Guillemin et al., 2000). Fluoroquinolone resistance in *M. tuberculosis* via expression of multi-drug efflux pumps has not been reported but is a common resistance mechanism in other bacteria (Poole, 2000).

In 2001, genetic selection for fluoroquinolone resistance in *M. smegmatis* identified a new fluoroquinolone resistance factor, the mfpA-encoded protein, which when present on a multi-copy plasmid resulted in low-level resistance (4-8 fold increase in MIC values) to ciprofloxacin and sparfloxacin (Montero et al., 2001). The sequence of MfpA revealed it to be a member of the "pentapeptide repeat" family of bacterial proteins (Bateman et al., 1998), in which every fifth amino acid is a hydrophobic residue, predominantly leucine and phenylalanine. *M. tuberculosis* contains a 184 amino acid MfpA homologue (MtMfpA), encoded by the Rv3361c gene, that is 67% identical to the 192 residue *M. smegmatis* MfpA protein. Hundreds of members of this family have been identified in bacterial genomes, including the McbG protein responsible for resistance to microcin B17 in *E. coli* (Garrido et al., 1998). This peptidic antibiotic also inhibits DNA gyrase (Heddle et al., 2001), although via a different mechanism of action (Pierrat and Maxwell, 2003). A third member of the pentapeptide repeat family is the 212 amino acid, plasmid-encoded Qnr protein, originally identified in quinolone-resistant strains of *Klebsiella pneumoniae* (Jacoby et al., 2003). This plasmid-encoded protein protects DNA gyrase against fluoroquinolone inhibition (Tran and Jacoby, 2002). The presence of Qnr homologues on transmissible plasmids in fluoroquinolone resistant clinical isolates of *Shigella* and *Enterobacteriae* has recently been reported in Japan (Hata et al., 2005) and Germany (Jonas et al., 2005).

Experimental

The *M. tuberculosis* Rv3361c open reading frame was PCR amplified from *M. tuberculosis* H37R$_v$ genomic DNA, ligated into a pET28a plasmid and expressed in an *E. coli* BL21 (DE3) strain transformed with the resulting plasmid. IPTG-induced expression yielded cell extracts containing a soluble protein band at ca. 20 kDa, and the enzyme was purified to homogeneity using Ni-NTA chromatography (Supplementary Material).

Figure 1:
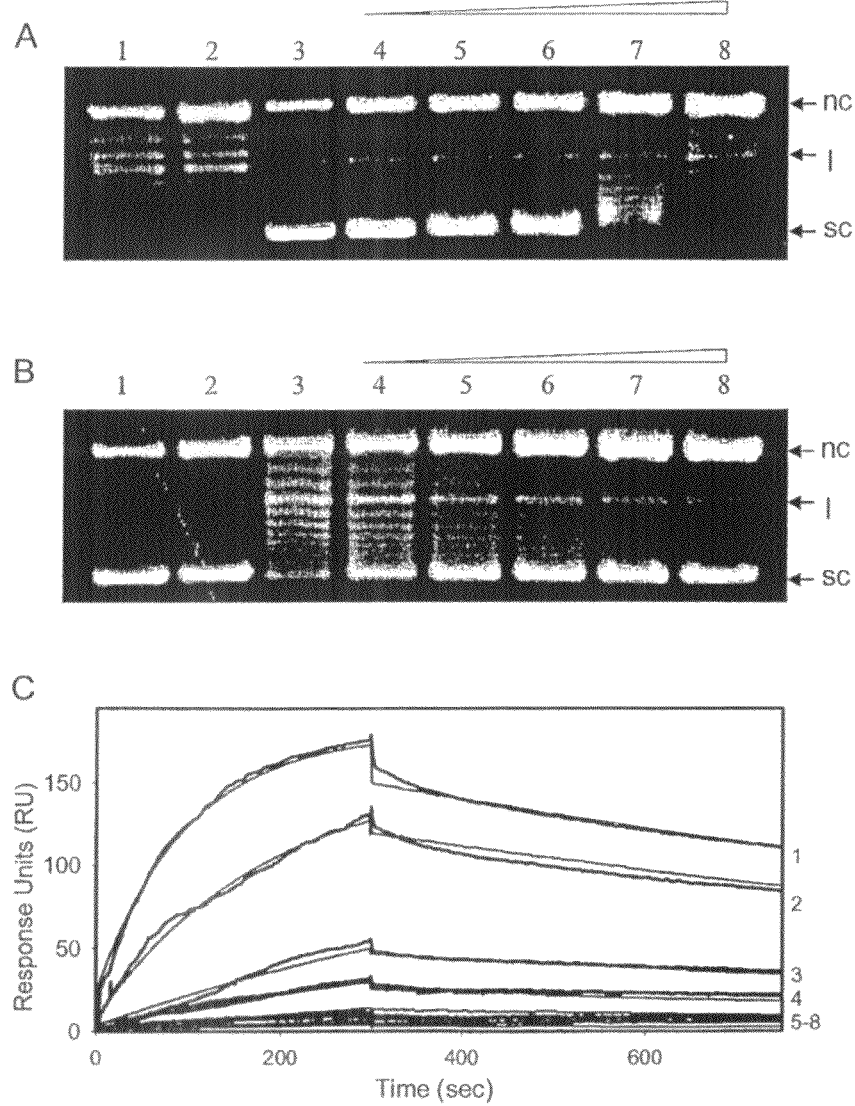
FIG. 1 is photographs and a graph of experimental results showing the effect of MfpA on *E. coli* DNA gyrase. Panels A and B show inhibition of supercoiling (A) and relaxation (B) activity of *E. coli* DNA gyrase by MfpA. Panel A. Lane 1, relaxed pBR322 alone; lane 2, pBR322 containing 5 µM MfpA; lane 3, 3 units of gyrase; lanes 4-9, 3 units of gyrase and 1, 2, 3, 5, and 8 µM MfpA, respectively. Panel B. Lane 1, supercoiled pBR322; lane 2, supercoiled pBR322 containing 5 µM MfpA; lane 3, supercoiled pBR322 with 25 units of gyrase; lanes 4-8, units of gyrase containing 1, 2, 3, 5 and 8 µM MfpA, respectively. nc, 1 and sc are nicked circular, linear and supercoiled forms respectively. Gyrase assays were performed as described previously. Panel C shows BIAcore sensorgrams of DNA gyrase binding to MfpA. DNA gyrase (1) 12 µM, (2) 6 µM, (3) 1.5 µM, (4) 0.75 µM in duplicate, (5) 0.375 µM in duplicate, (6) 0.188 µM, (7) 0.094 µM and (8) the buffer alone were injected to immobilized MfpA as described and the sensograms were recorded. Symbols (●) are experimentally recorded values while thin lines (-) are a fit of the data to 1:1 Langmuir model.

The heterologously expressed, homogeneous protein was tested for its ability to prevent the inhibition of recombinant *E. coli* DNA gyrase by ciprofloxacin, as this had been reported for the related Qnr protein (Tran and Jacoby, 2002). As a control, the effect of MfpA alone on both ATP-dependent DNA supercoiling and ATP-independent relaxation reactions catalyzed by *E. coli* DNA gyrase was tested. MtMfpA inhibited both reactions in a concentration dependent manner (FIGS. 1A&B). The apparent IC$_{50}$ values were calculated to be ca. 1.2 µM (based on an active dimer, see below) for both reactions. To distinguish between indirect effects on catalysis or the direct interaction of MfpA with gyrase, surface plasmon resonance experiments (BIAcore) were performed using standard amine coupling of MfpA to CM5 sensor chips. Increasing concentrations of gyrase were flowed over the chip, and the signal measured. The signal was saturable and allowed us to calculate a K$_d$ value of 460 nM from the ratio of k$_{on}$ and k$_{off}$ values of ~$10^3$ M$^{-1}$ sec$^{-1}$ and ~$10^{-4}$ sec$^{-1}$, respectively (FIG. 1C). These values are in approximate agreement with the IC$_{50}$ values obtained for gyrase inhibition, indicating that MfpA interacts directly with DNA gyrase.

MfpA was crystallized using vapor diffusion under oil, and both native and selenomethionine-substituted proteins were crystallized in several space groups that diffracted to 2.0-2.7 Å. Diffraction data on selenomethionine-substituted protein crystals in space group P3$_2$21 were collected at three wavelengths. Higher resolution data from the native protein in the P2$_1$ crystal form were added to extend the phases, and improve the quality of the maps. The final structure has been refined to 2.0 Å (Table 1).

TABLE 1

Data collection and Refinement Statistics

| Data Collection | |
| --- | --- |
| Space Group | P2$_1$ |
| Unit Cell Dimensions | a = 53.8, b = 31.0, c = 96.8 Å, β = 93.2° |
| Maximal Resolution | 2.0 Å (2.0-2.07) |
| Completeness | 98.8 (95.8) % |
| Rmerge | 3.2 (16.1) |
| I/σ(I) | 18.3 |
| Redundancy | 4.4 |
| Refinement Statistics | |
| Model | A1-A183, B1-B180 205 H$_2$O, 1 SO$_4$ |
| Rwork/Rfree | 17.7 (16.6)/21.8 (22.2) |
| RMS Bond/Angle | 0.021 Å/1.89° |
| Mean B-factor Protein/Nonbonded | 18.7/28.9 |

[1]Statistics for highest bin in parentheses

Figure 2:
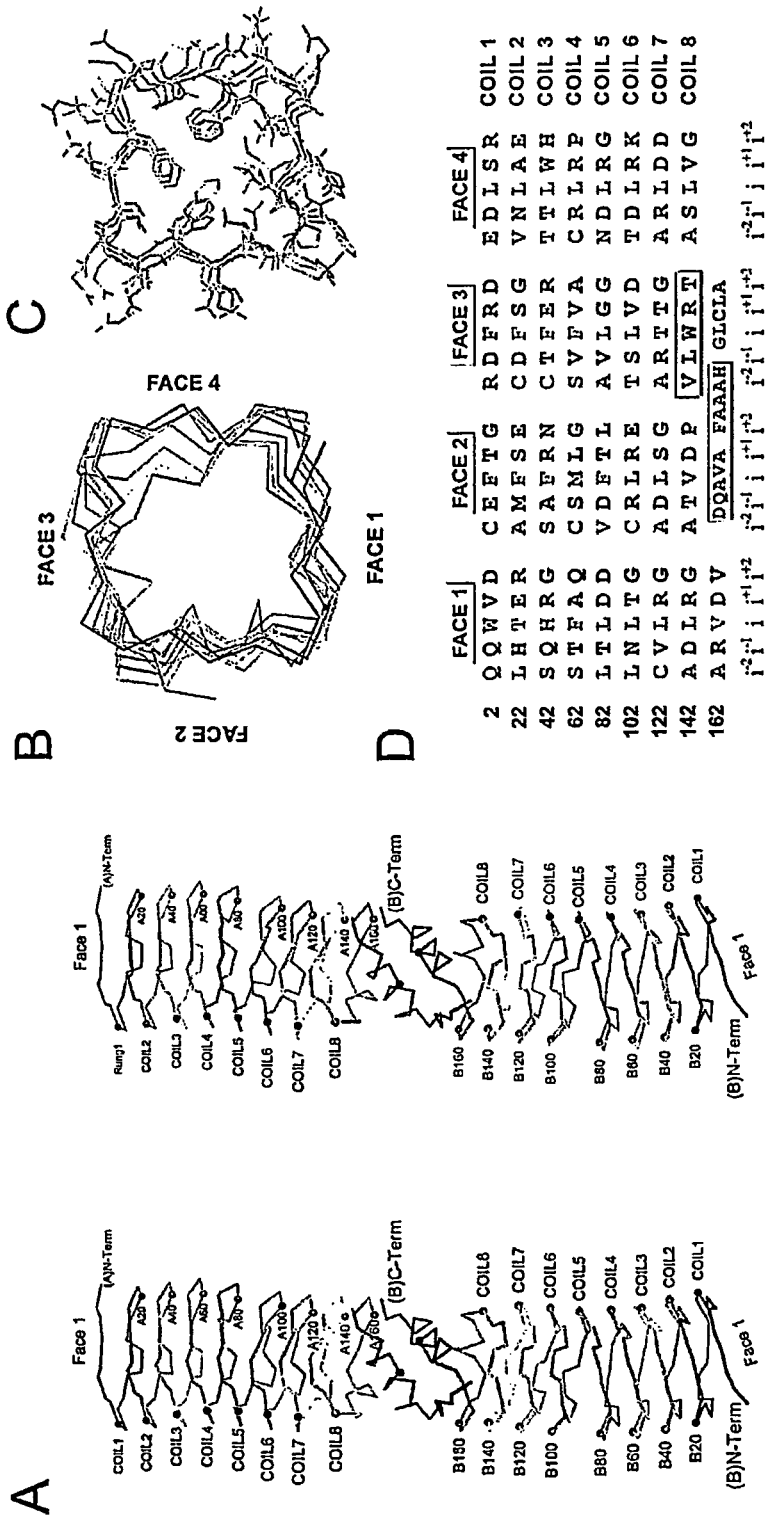
FIG. 2 shows MfpA Structural Fold Illustrations. Panel A shows stereo-view of the Cα trace of MfpA dimer shown with the monomers colored from blue (N-terminus) to red (C-terminus). Every $10^{th}$ Cα is shown as a small sphere. Every $20^{th}$ residue is labeled. Panel B shows a Cα trace, from N-terminus to C-terminus, viewed down the helical axis of an MfpA monomer. Panel C show a stick representation of residues 2-81 (coils 1-4), looking down the helical axis, colored by atom type. Panel D shows the amino acid sequence of MfpA (SEQ ID NO:1). The two C-terminal helices are boxed.

MfpA is a dimer in solution (data not shown) and in the crystal, with the C-terminal α-helices interacting with the C-terminal α-helices of the other monomer. The MfpA monomer is almost entirely comprised of a right-handed β-helix (FIG. 2A; residues 2-165 of a total of 185 residues). The right-handed β-helix has eight complete coils, each with four nearly equivalent sides, giving the core of the structure a quadrilateral appearance (FIG. 2B). The coils are stacked upon each other with only a slight left handed twist. Each of the sides is coded by one of the pentapeptide-repeating units with the middle hydrophobic residue (i) and first small polar/hydrophobic residue (i$^{-2}$) pointing inwards and the remaining residues (i$^{-1}$, i$^{+1}$, and i$^{+2}$) pointing outwards (FIG. 2C, D). There is extensive hydrogen bonding interaction between the peptide backbone atoms of neighboring coils, including in the turns, although only the i$^{+1}$ residue is consistently in a full parallel beta-strand interaction. Every 20 residues the right-handed β-helix completes a revolution and travels ~4.8 Å along the helical axis. The core of the β-helix is devoid of water, but is not entirely hydrophobic in nature. Where there are violations of the hydrophobic nature of the i residue, a compensatory polar residue is positioned nearby to which it hydrogen bonds. For example, the side chains of Thr24 and His44 (i position residues in coils 2 and 3, respectively) are on consecutive coils on the same face and form a hydrogen bond. In addition His44 also forms a hydrogen bond with the side chain Ser42 at the i$^{-2}$ position. Where there is a small polar residue at position i$^{-2}$, its side chain typically points into the corner of the quadrilateral and forms hydrogen bond(s) with backbone amides or carbonyls of its own adjacent turn or with that of turns above or below its position. Where the small polar/hydrophobic residue at position i$^{-2}$ rule is broken, this requires compensatory changes nearby to allow for a larger residue. For example, Asn97 and Leu102 are allowed at the i$^{-2}$ position because the helical axis tilts here creating a larger separation between coils 4 and 5 on face 3 and 4. This tilt is caused by the presence of Pro81 between faces 3 and 4 that leads to a disruption of the hydrogen bonding between coils 4 and 5 and a change in the helical axis of coils 1-4 and 5-8 of 12 degrees. There are several tightly bound water molecules that accommodate the open hydrogen bonds thus created.

Both the N- and C-termini of the β-helix are capped by tryptophan residues in the i position (Trp 4 and Trp154). The C-terminal twenty residues appear as a two-turn (α1) and a three-turn (α2) helix, with the former occupying the place of the face 3 β-strand of coil 8. The C-terminal α2 helices interact in an antiparallel manner to generate a hydrophobic dimer interface that is observed in all four crystal forms, and the molecular two-fold axis. The dimer is highly asymmetric and rod-shaped, with a length of ~100 Å and a diameter of 27 Å at the N-termini and 18 Å at the dimer interface. While the Cα atoms form a perfectly square quadrilateral down the long axis, the outward-facing side chains of the i$^{-1}$, i$^{+1}$ and i$^{+2}$ residues produces a protein surface with a more cylindrical shape when viewed down the helical axis. All of the charged residues (19 Arg, 1 Lys, 18 Asp, 7 Glu) are located at these positions, generating a dimer with an overall charge of −10. However, the charge distribution is not uniform, and there is a distinct negative potential due to residues on face 1 and face 2 along the length of the molecule (FIG. 3A). The right-handed helical nature of the fold, the dimensions and shape of the dimer, and the negative electrostatic surface potential suggested that MfpA might be mimicking a 30-35 base pair segment of B-form duplex DNA, and could be capable of interacting directly with DNA gyrase. This is a new fold, and there are no structures in the Protein Database that share significant similarity to MfpA.

Using a rigid body docking approach, the structures of the MfpA protein and the N-terminal domain of the *E. coli* gyrase A subunit (GyrA59; Morais Cabral et al., 1997) could be readily docked, without significant steric clashes, to provide electrostatic complementarity between the highly cationic "saddle" at the $A_2$ dimer interface, thought to be the position where DNA binds and is cleaved, and the highly anionic surface of the MfpA dimer (FIG. 3B). The MfpA dimer extends across the entire GyrA dimer, providing an explanation for its powerful inhibition of gyrase activity. This model suggests that MfPA will compete with B-form DNA for the gyrase surface. Since fluoroquinolones bind only to the DNA gyrase-DNA complex (Wilmot and Maxwell, 1993), preventing the formation of this complex provides a molecular explanation for the resistance phenotype. Additional support for this mechanism comes from the recent report that the related fluoroquinolone resistance factor, Qnr from *Klebsiella pneumoniae*, competes with DNA for DNA gyrase (Tran et al., 2005).

Discussion

DNA mimicry by proteins has been reported for the interaction of TAF$_{II}$230 with the TATA binding protein, TBP (Liu et al., 1998). In this case, the globular TAF$_{II}$230 binds to TBP as a mimic of the minor groove of unwound DNA. DNA mimicry has also been invoked in the structure of highly acidic 107 amino acid residue HI1450 protein from *Haemophilus influenzae* (Parsons et al., 2004). The structure of this protein consists of a central 4-stranded beta sheet containing two alpha helices on one face of the sheet. It bears some overall structural similarity to the gyrI-encoded DNA gyrase inhibitor (Nakanishi et al., 2002) that protects cells from Microcin B17 (also referred to as SbmC), whose structure has also been solved by crystallographic methods (Romanowski et al., 2002). The bacteriophage T7 Ocr protein, whose three-dimensional structure (30) reveals an all α-helical protein that forms end-to-end dimers with a distinct surface anionic charge has also been suggested to mimic the surface charge distribution of DNA. However, MfpA is folded into an unprecedented structure that is itself a right-handed helix with a size, shape and charge distribution strikingly reminiscent of B-form DNA.

It appears likely that the other members of this large bacterial family of pentapeptide repeat proteins (Pfam: pf00805, 31) will adopt a similar overall fold, although the surface charge distribution could vary widely. In *Anabena* and *Synectocystis* species, there are over twenty genomically-encoded pentapeptide family members. The *Anabena* HglK protein contains four N-terminal membrane spanning sequences and a C-terminal pentapeptide repeat (Black et al., 1995) and has been proposed to direct the localization of glycolipids to the membrane during heterocyst formation, although the function of the pentapeptide domain is unclear. In *E. coli*, the McbG protein is part of the microcin B17 biosynthetic gene cluster, and protects against the action of the antibiotic, possibly by binding to DNA gyrase in a manner similar to that of MfpA and preventing microcin B17 binding. Finally, the plasmid-encoded oxetanocin A biosynthetic gene cluster of *Bacillus megaterium* also contains a pentapeptide repeat protein (Morita et al., 1999) that may prevent this potent inhibitor of viral DNA polymerases and HIV reverse transcriptase (Izuta et al., 1992) from inhibiting the host polymerase, analogous to the McbG protein.

The physiological role that might be played by the MfpA family of proteins in the various organisms in which they are found is not yet clear. While *M. tuberculosis* contains a single type II topoisomerase that is inhibited by MfpA, other microorganisms contain multiple proteins that assist in topological rearrangements of DNA. MfpA-like proteins might coordinately regulate proteins that bind to, or metabolize, DNA. In *M. tuberculosis*, expression of MfpA may be coordinated with cell replication. Such coordination would provide DNA topological assistance when needed, but prevent undesired topological changes during periods of replicative senescence. This repression of topoisomerase activity would thus contribute to the maintenance of the condensed chromosome. Viewed in this regulatory context, the proposed mechanism of coordinate regulation of the interaction of DNA binding proteins and DNA would require additional mechanisms that would either control expression of MfpA or modulate its activity.

DNA binding proteins are notable for presenting large patches of positive potential on their surfaces. Inspection of FIG. 3A immediately suggests that pentapeptide repeat proteins with their complementary negative surface potentials and DNA-like proportions will prove to be a general class of inhibitors of DNA binding proteins, similar to MfpA and DNA gyrase. In addition, bacterial pentapeptide repeat proteins can be identified linked to other domains, like the HglK protein, that are homologous to bacterial enzymes with phosphorylation and acetylation activities, and may target these activities to DNA binding proteins. Finally, the core of the right-handed quadrilateral β-helix structure appears robust enough to allow for surface amino acid substitutions that could tailor specificity, and could provide a platform for the rational design of novel proteins that specifically target DNA-binding proteins of known structure.

Materials and Methods

Cloning, Expression and Purification of MfpA.

The Rv3361c open reading frame was PCR amplified using *M. tuberculosis* H37Rv genomic DNA as template and cloned into pET28a vector as an NdeI/BamHI fragment. Recombinant protein bearing a cleavable $NH_2$-terminal $His_6$ tag was expressed in *E. coli* BL21 (DE3) strain, harboring the plasmid pGroESL-911 that expresses the molecular chaperone GroES/GroEL (Ichetovkin et al., 1997) at 20° C. Recombinant MfpA was purified to homogeneity using Ni-NTA chromatography and the $His_6$ affinity tag was removed by digesting with thrombin. Seleno-Met labeled protein in *E. coli* 834 (DE3) strain harboring pGroESL plasmid using SelenoMet medium (Anatrace Inc., Maumee, Ohio) was expressed and purified as described above. A second plasmid was constructed by cloning PCR amplified Rv3361c orf into pQE12 (Qiagen) vector as an EcoRI/BamHI fragment. Expression of the protein in *E. coli* XL1 Blue strain, harboring the plasmid pGroESL-911 was performed at 20° C. The soluble MfpA protein was purified using three consecutive chromatographic steps employing phenyl sepharose, anion exchange on MonoQ and gel filtration on Superdex-75 matrices. Trace amounts of nuclease activity associated with the protein preparation was removed by heat treatment at 62° C. for 10 min. The apparent molecular weight of 20 kDa, as determined by SDS-PAGE was in agreement with the weight calculated from the gene sequence. DNA sequencing of the cloned fragments confirmed the absence of any mutations introduced during PCR amplification. The final preparations were found to be homogeneous as determined by SDS-PAGE.

Gyrase Assays.

DNA gyrase assays (ATP dependent supercoiling and ATP-independent relaxation) were performed as described (Ali et al., 1993; Mizuuchi et al., 1984; Reece and Maxwell, 1989).

Surface Plasmon Resonance (BIAcore) Analysis.

Biosensor studies were performed on a BIAcore 3000 instrument (BIAcore, Inc.; Piscataway, N.J.). MfpA was covalently immobilized on censor chip CM5 using amine coupling according to manufacturer's protocol. Typically 50-150 response units (RU) were immobilized on individual flow cells of the sensor chip. Analyte, *E. coli* DNA gyrase (12, 6, 3, 1.5, 0.75, 0.375, 0.188, 0.094 and 0.047 μM) in 35 mM Tris buffer, pH, 7.5 containing 6.5% glycerol, 4 mM $MgCl_2$, 25 mM KCl, 5 mM DTT and 100 μg/ml BSA was injected for 5 min at a flow rate of 30 μl/min using the kinject command. Association and dissociation kinetic constants were calculated by BIAevaluation 3.1 software using a simple 1:1 Langmuir model.

Crystallization. MfpA was concentrated to 5-10 mg/ml and stored in 10 mM Tris pH 7.5, 1% ethylene glycol, 30 mM β-ME. Four unique crystal forms of MfpA were obtained by vapour diffusion under oil. In general, 2 μl of MfpA was combined with 2 μl of crystallization solution under 100 μl of FISHER silicon oil, and incubated at room temperature. Prior to data collection crystals were immersed in a cryogen and vitrified by immersion in liquid nitrogen. The crystallization solutions and cryogen solutions were—C2 Form: 30% Peg400, 100 mM $(NH_4)_2$HCitrate pH 5.5, cryogen—same. $P2_1$ Form: 30% Ethylene Glycol, 100 mM citrate phosphate pH 5.5, 200 mM $(NH_4)_2SO_4$, cryogen—30% ethylene glycol, 100 mM MES pH 5.2, 200 mM $(NH_4)_2SO_4$. C222, Form: 35% 2-ethoxyethanol, 100 mM $Na_3$Citrate pH 5.5, cryogen—30% Peg400, 100 mM MES pH 5.2, 11.0M CsCl. $P3_221$ Form: 30% ethylene glycol, 100 mM citrate phosphate pH 4.5, 200 mM $(NH_4)_2SO_4$, cryogen—25% ethylene glycol, 100 mM citrate phosphate pH 4.5, 100 mM $(NH_4)_2SO_4$.

Data Collection and Phasing. Selenomethionine MfpA was purified and crystals of the $P3_221$ crystal form were obtained in the same manner as wild type. A three wavelength multiple anomalous dispersion (MAD) experiment was performed at the selenium edge on the X9A beamline at Brookhaven National Laboratories (Table 2). The positions of the selenium atoms were located and density modified phases were calculated using the program SOLVE/RESOLVE (Terwilliger et al., 2002). The resultant map was of sufficient quality to locate the three MfpA molecules per asymmetric unit and the non-crystallographic symmetry operators. Improvement of the SOLVE phases by density modification was redone within the program DM (Cowtan, 1994) with the inclusion of three fold averaging to obtain a much improved map. A majority of the structure was auto-fit into the $P3_221$ MAD/DM map using the program ARP/WARP (Perrakis, 1997) while a minority was fit manually. This intermediate structure was used as a molecular replacement model to solve the C2 crystal form, which, since it was of higher quality, was used in subsequent rounds of rebuilding and refinement. The C2 crystal form, and all other datasets excluding the MAD data, were collected at 125 K on an R-Axis IV++ imaging plate detector mounted on a Rigaku RU-H3R generator equipped with Osmic Blue optics and operating at 50 kV and 100 mA. The HKL package (Otwinski, 1993) was used to integrate and scale all datasets. A complete listing of data collection statistics is shown in Table 2 and 3. Molecular replacement calculations utilized the program AMORE (Navaza, 2001). All refinement and rebuilding utilized the programs CNS (Brunger et al., 1998) and O (Jones, 1978), respectively. A complete listing of refinement statistics is shown in Table 2 and 3. Electrostatic calculations were performed using the programs GRASP (Nichols et al., 1993).

TABLE 2

MAD Data Collection and Phasing Statistics[1,2]

| Data Set | Peak | Inflection | Remote |
|---|---|---|---|
| Wavelength, Å | 0.97931 | 0.97954 | 0.96423 |
| Space Group | | $P3_221$ | |
| Unit Cell Dimensions | | a = 83.6 Å, c = 147.7 Å | |
| Maximal Resolution, Å | 3.2 (3.2-3.31) | 2.3 (2.3-2.38) | 2.3 (2.3-2.38) |
| Completeness, % | 100.0 (100) | 99.9 (100) | 99.9 (100) |
| Rmerge | 4.4 (18.6) | 4.2 (12.3) | 4.4 (13.9) |
| I/σ(I) | 14.2 | 12.7 | 14.4 |
| Redundancy | 11.8 | 11.7 | 11.8 |

[1]Bijvoets not merged
[2]Statistics for highest bin in parentheses

TABLE 3

Data Collection and Refinement Statistics[1]

| | mfpA03 | mfpA09 | mfpA11 |
|---|---|---|---|
| | Data Collection | | |
| Space Group | C2 | $C222_1$ | $P3_221$ |
| Unit Cell Dimensions | a = 177.2 Å, | a = 33.4 Å, | a = 84.1 Å, |
| | b = 31.1 Å, | b = 48.6 Å, | c = 147.1 Å |
| | c = 69.6 Å, | c = 188.4 Å | |
| | β = 111.4° | | |
| Maximal Resolution | 2.2 Å (2.2-2.28) | 2.2 Å (2.2-2.28) | 2.7 Å (2.7-2.8) |
| Completeness, % | 93.3 (85.5) | 97.1 (92.3) | 94.0 (90.5) |
| Rmerge | 3.0 (13.0) | 6.5 (13.8) | 3.4 (18.0) |
| I/σ(I) | 18.4 | 18.4 | 18.4 |
| Redundancy | 2.6 | 6.4 | 4.5 |
| | Refinement Statistics | | |
| Model | A1-A183 | A3-A180 | A1-A180 |
| | B1-B183, 51 | 69 $H_2O$ | B1-B180 |
| | $H_2O$ | 3 Cs | C1-C180 |

TABLE 3-continued

Data Collection and Refinement Statistics[1]

|  | mfpA03 | mfpA09 | mfpA11 |
|---|---|---|---|
| Resolution | 2.2 Å | 2.2 Å | 2.7 Å |
| Rwork/Rfree | 21.8/26.9 | 19.9/25.2 | 25.3/29.5 |
| RMS Bond/Angle | 0.018 Å/1.84° | 0.024 Å/2.14° | 0.008 Å/1.30° |
| Mean B-factor Protein/Nonbonded | 28.7/35.6 | 19.7/27.0 | 30.6/— |

[1]Statistics for highest bin in parentheses

Example 2

Cloning, Expression and Purification of *Nostoc punctiforme* Pentapeptides (NP0275 and NP 0275/0276)

The NP0275 open reading frame was amplified using *Nostoc punctiforme* genomic DNA by standard PCR techniques using the oligonucleotides NpPF (5'-ATCCCGCT<u>CATATG</u>GACG TAGAAAAACTCAGG-3') (SEQ ID NO:4) and NpPR (5'-ATCCCGCT<u>AAGCTT</u>CTAATTTAAAACGGCTT CAT C-3') (SEQ ID NO:5) containing the underlined NdeI and HindIII restriction sites shown, respectively. The PCR product was cloned into pET-28a vector, transformed into *E. coli* strain BL21(DE3) and selected on a Luria Broth (LB) agar plate containing 30 μg/ml kanamycin. DNA sequencing of the cloned fragment was carried out to confirm the absence of any mutations introduced during PCR amplification.

For shake flask growth, 1 liter of LB medium supplemented with kanamycin (30 μg/ml) was inoculated with 10 ml of overnight culture and incubated at 37° C. The culture was grown to mid log phase ($A_{600}$~0.8), induced with 0.5 mM isopropyl thio-β-D-galactoside, and further incubated for 4-6 h. Cells were harvested by centrifugation, resuspended in buffer A (50 mM Tris buffer, pH 7.5, containing 10 mM imidazole and 250 mm NaCl), lysed by sonication and cell debris was removed by centrifugation at 18000 rpm for 30 min. The supernatant was then loaded onto buffer A equilibrated Ni-NTA column, washed with buffer A and the bound protein was eluted using a linear gradient of 0-300 mM imidazole in buffer A. Fractions containing the pure protein (as determined by SDS-PAGE) were pooled, the protein was precipitated by ammonium sulfate at 85% saturation and collected by centrifugation. Precipitated protein was redissolved in 50 mM Tris buffer, pH 7.5, and dialyzed extensively against the same buffer.

Cloning and Expression of NP0275/0276.

Figure 4:
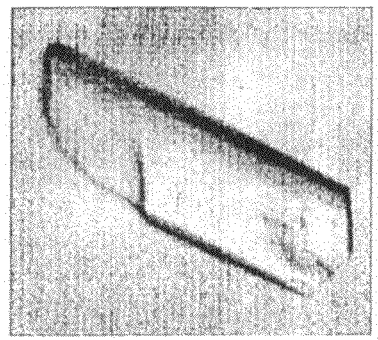
FIG. 4 shows the C-terminal pentapeptide repeat and other information of *Nostoc punctiforme* protein NP0275 (SEQ ID NO:2).
Figure 5:
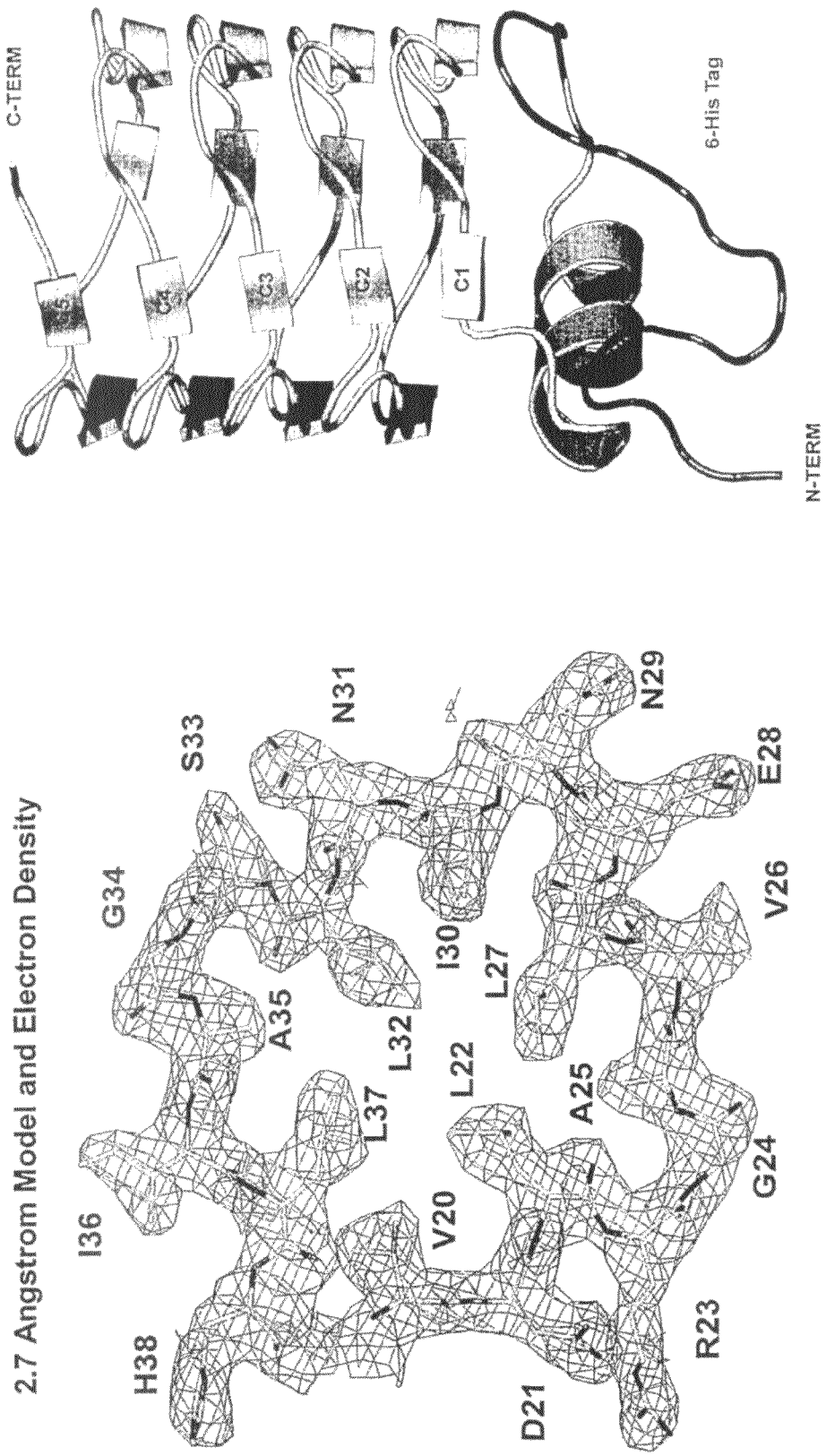
FIG. 5 shows the structure of NP0275.
Figure 7:
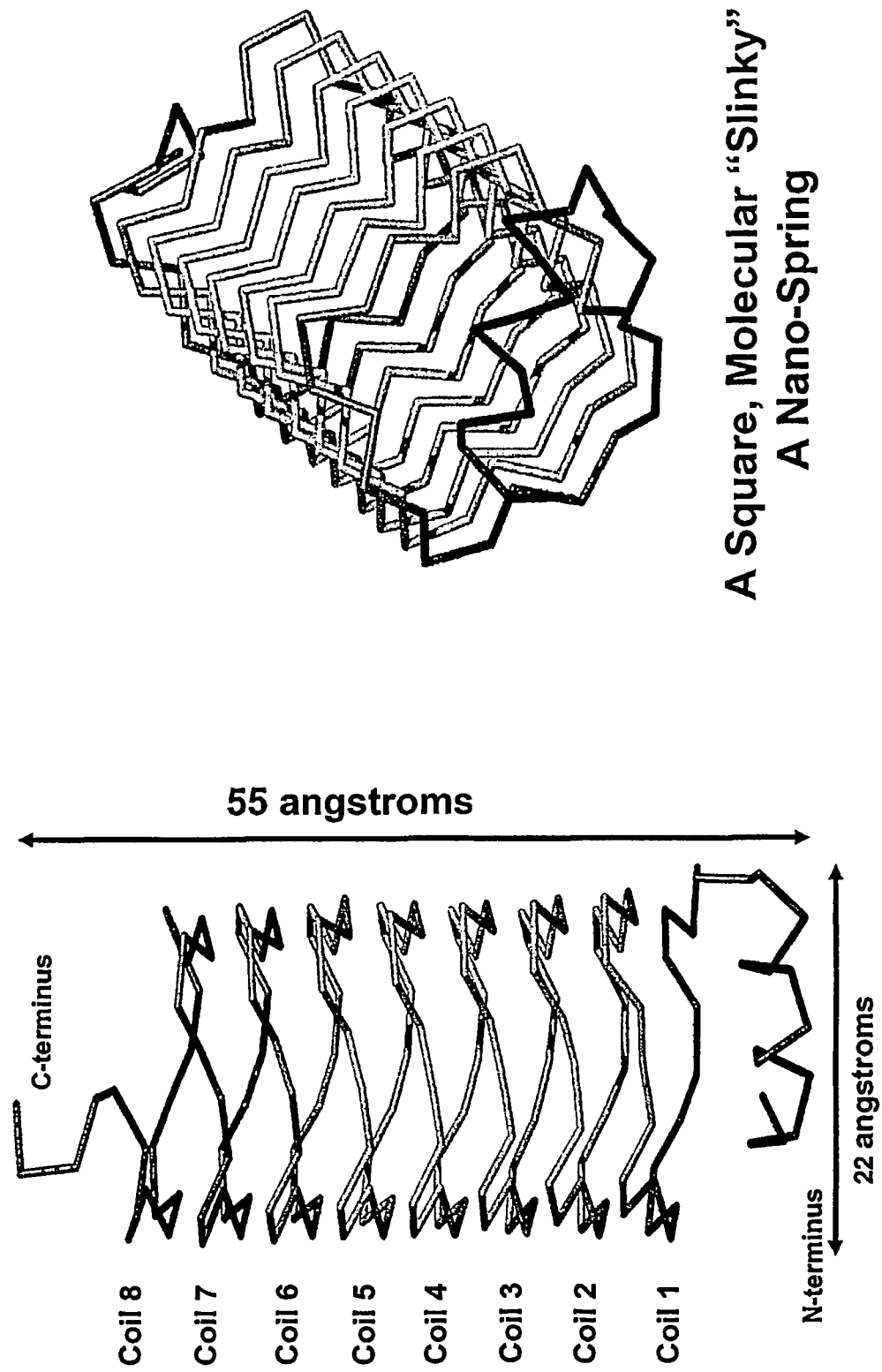
FIG. 7 shows a model of the *N. punctiforme* NP0275/0276 fusion protein.
Figure 8:
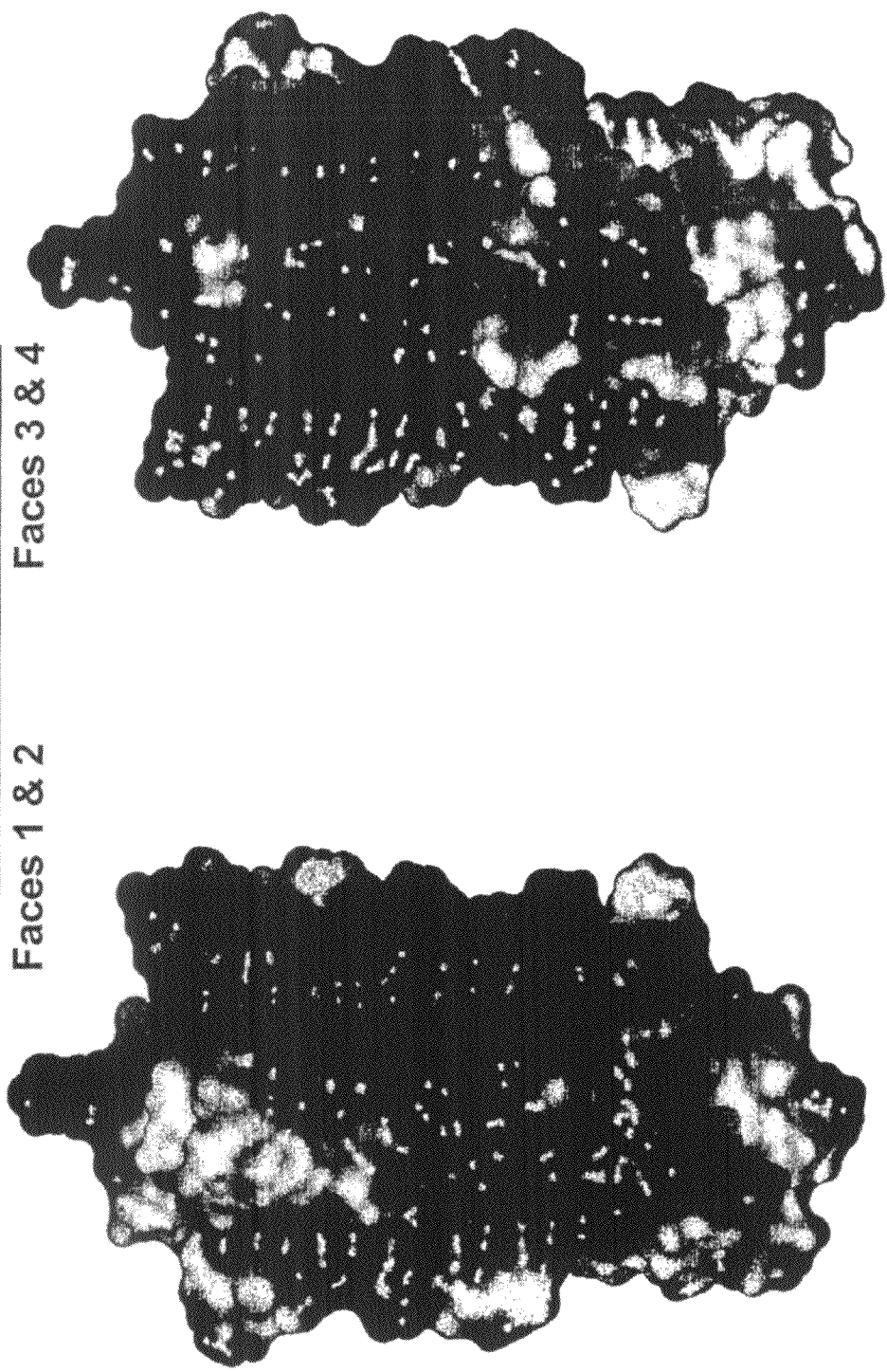
FIG. 8 shows a model of NP0275/0276 showing the electrostatic surface of that fusion protein.
Figure 9:
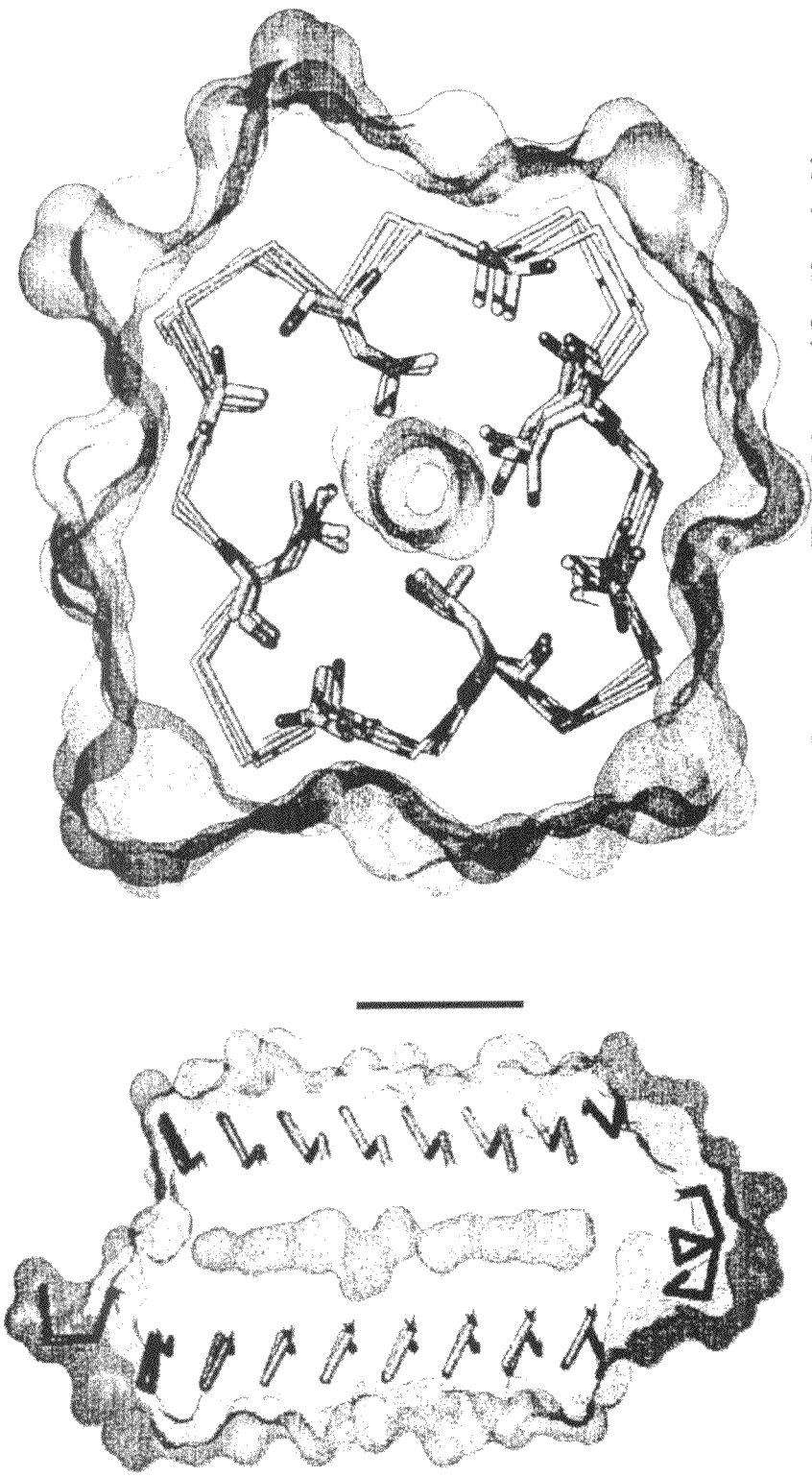
FIG. 9 shows cutaway models of NP0275/0276 showing an internal cavity of that fusion protein.

The full-length open reading frames of NP 0275 plus 0276 was PCR amplified and cloned into pET 28a as described above. The stop codon at the end of NP0275 was mutated to Gln (TAG→CAG) using the QuikChange® Site-Directed Mutagenesis Kit (Stratagene). Resultant construct expressed NP0275/0276 fusion protein. DNA sequencing of the resultant construct yielded the desires sequence. The fusion protein was expressed and purified as described above. An additional Superdex S75 gel filtration chromatography was used to get the homogeneous protein preparation as determined by SDS-PAGE. The deduced amino acid sequence of the pentapeptide repeat from NP0275 is shown in FIG. 4.

Neither 0275 nor 0275/0276 exhibited any significant inhibition against DNA gyrase.

Example 3

Crystallization and Structure Determination of the Pentapeptide Repeat Proteins Np0275 and Np0275/0276 from *Nostoc punctiforme*

Crystallization.

Solution conditions that yielded crystals of Np0275 and Np0275/0276 were discovered using commercially available crystallization screens and vapor diffusion under oil. Typically, 2 μl of purified protein was combined with 2 μl of crystallization reagent under 150 μl of silicon oil. The crystallization plates were stored at 18° C. with the oil exposed to room humidity. Initial crystallization hits were refined using vapor diffusion under oil, and the resultant crystals checked for suitable diffraction. All crystallographic data were collected on a MSC R-Axis IV++ image plate detector using CuKα radiation from a Rigaku RU-H3R x-ray generator and processed using MOSFLM (Leslie, 2006). All protein preparations used in structure determination retained the 20 amino acid hexahistadine thrombin cleavable tag.

Np0275.

Np0275 (25 mg/ml, 10 mM Tris pH 8.0) crystallized in 20-30% PEG 3350 (w/v), 100 mM NaCacodylate pH 6.8, 200 mM LiCl. Crystals grew as rods over 2-7 days with maximum dimensions of 0.3×0.1×0.1 mm. Crystals were soaked in 40% PEG3350 (w/v), 100 mM NaCacodylate pH 6.8, 200 mM LiCl prior to vitrification in liquid nitrogen. Crystals of NP0275 belong to the orthorhombic space group $P2_12_12_1$ with unit cell dimensions of a=29.3, b=63.2, c=100.7 Å. Solvent content analysis suggested one (67.2% solvent) or two (34.3% solvent) molecules per asymmetric unit.

Np0275/0276.

Np0275/0276 (10 mg/ml, 5 mM Tris pH 8.0, 33 mM NaCl) crystallized in 2.0-3.0 M $(NH_4)_2SO_4$, 100 mM MES pH 6.5. Distorted bipyramidal shaped crystals grew over 1 to 2 weeks in drops that had undergone a large depletion in volume by evaporation, and obtained maximum dimensions of 0.5×0.4× 0.4 mm. Crystals were soaked in 3.5 M $NH_4)_2SO_4$, 100 mM MES pH 6.5 prior to vitrification in liquid nitrogen. Crystals of NP0275/0276 belong to the orthorhombic space group $P2_12_12_1$ with unit cell dimensions of a=49.6, b=55.5, c=59.0 Å. There is 1 molecule per asymmetric unit with a solvent content of 33.8%

Structure Determination

NP0275.

A molecular replacement model of NP0275 consisting of residues 20 through 98 (approximately four coils) was built utilizing the N-terminal coils of the pentapeptide repeat protein MfpA (Hegde et al., 2005) from *Mycobacterium tuberculosis*. The N-terminal coils of MfpA have a similar sequence composition as NP0275; in particular the central residues are almost always a leucine. In addition, the structure of MfpA provided various rules for the precise conformation of side chains depending on which position in the pentapeptide they occur. This permitted the construction, with reasonable accuracy, of a model of Np0275 with the correct sequence. The program MOLREP (Vagin et al., 2000) produced two independent molecular replacement solutions utilizing the NP0275 model. Neither of the individual solutions was able to generate a complete packing solution, however; in combination the two solutions generated reasonable crystal contacts suggesting that there are two monomers per asymmetric unit. These two solutions were converted into polyalanine models and underwent rigid body refinement in REFMAC (Murshudov et al., 1007). Electron density maps generated using the rigid body polyalanine model for phasing showed obvious density for sidechains consistent with the 'correctness' of the molecular replacement solution. Attempts to refine the original molecular replacement model did not produce a reasonable drop in the Rfree. Inspection of the maps indicated that one of the molecular replacement solutions was out of register by one pentapeptide repeat (structure was rotated 90° incorrectly). Several rounds of manual model building within the molecular graphics program COOT (Emsley, P. and K. Cowtan, 2004) followed by refinement in REFMAC resulted in a refined structure with an Rfactor and Rfree of 0.194 and 0.253 respectively (see Table 4). There was sufficient electron density to model all of the residues predicted by the genomic sequence (residues 1-98). In addition, a total of 27 residues from the N-terminal cleavable his-tag, 9 from monomer A, and 18 from monomer B were also modeled.

Np0275/0276.

Initial phases for the Np0275/0276 dataset were obtained utilizing residues 1-98 of Np0275 as a molecular replacement model in the program AMORE (Navaza, 1994). The majority of the model was built by the automated fitting and phasing program ARPWARP (Perrakis, 1997), yielding a starting model containing residues 1-174 with an $R_{factor}$ and $R_{free}$ of 0.245 and 0.273 respectively. The remainder of the structure was built with the molecular graphics program COOT, and refined in REFMAC to an Rfactor of 0.182 and Rfree of 0.190, respectively (see Table 4). The final model contains all of the native genomic sequence except 3 C-terminal residues, and includes 7 residues from the N-terminal cleavable His-tag.

Various characteristics of this fusion protein are illustrated and summarized in FIGS. 5-9.

TABLE 4

Data Collection and Refinement Statistics

|  | Np0275 | Np0275/0276 |
|---|---|---|
| Space Group | $P2_12_12_1$ | $P2_12_12_1$ |
| Resolution (Å) | 20-2.1 (2.27-2.10) | 20-1.5 (1.58-1.50) |
| Completeness (%) | 100 (100) | 99.8 (99.8) |
| Redundancy | 5.6 (5.7) | 4.8 (4.6) |
| Mean(I)/sd(I) | 23.6 (8.1) | 31.8 (11.2) |
| $R_{sym}$ | 0.053 (0.169) | 0.034 (0.116) |
| Model and Refinement Data | | |
| Resolution (Å) | 20-2.1 (2.16-2.10) | 20-1.5 (1.54-1.50) |
| Unique Reflections | 10813 | 25323 |
| $R_{cryst}$ | 0.194 (0.216) | 0.182 (0.308) |
| $R_{free}$ | 0.253 (0.252) | 0.190 (0.303) |
| Model Composition | | |
| Atoms total | 1754 | 1548 |
| Waters | 103 | 144 |
| Other | 1 Cl | 1 MES |
| Residues | A(−8) to A98 | A(−6) to A175 |
|  | B(−17) to B98 | |
| Average B-factor | | |
| Protein | 19.2 | 12.2 |
| Waters | 20.9 | 24.7 |
| RMSD | | |
| Bond lengths | 0.008 | 0.008 |
| Bond angles | 1.110 | 1.148 |

General Notes

The N-terminal end of Np0275 is capped by an α-helix, with the first coil starting at R15.

The C-terminal coil of Np0275 contains no capping residues, and has an exposed hydrophobic surface due to the exposed internal residues.

The sequence of Np0276 and the structure of Np0275/Np0276 suggest that Np0276 would not have a capped N-terminus.

The C-terminal coil of Np0276 is partially capped by residues 170-181 which do not conform to the pentapeptide signature, and extend perpendicular to the helical axis.

Np0275/0276 has a total of 8.5 coils.

The major differences between MfpA and Np0275/0276

The sequence of Np0275/0276 is much less variable and diverse than that seen in MfpA. Np0275/0276 has almost exclusively leucine at the 'i' position and alanine at the $i^{-2}$ position while MfpA has a mixture of phenylalanine, and leucine at the 'i' position and serine, threonine, cysteine, and alanine at the $i^{-2}$ position.

There is a change in the helical axis in MfpA at coils 5/6 due to residues which do not conform to the pentapeptide repeat consensus. The helical axis of Np0275/0276 is very uniform.

The coils of MfpA are composed of a mixture of type II and type IV turns resulting in variations in the diameter of the coils. The coils of Np0275/0276 are completely composed of type II turns and are very uniform.

There is a continuous cavity at the center of Np0275/0276 from the N-terminal coil to the C-terminal coil. MfpA has several smaller disjointed cavities.

MfpA is a dimer, Np0275 and Np0275/0276 are monomeric.

The major similarities between MfpA and Np0275/0276

Each has an overall negative charge, predominately due to the preponderance of residues in the $i^{-1}$ position to be aspartates.

While residues in the i−1, i+1, and i+2 (outer facing residues) have definite sequence preferences that are due to influences by the β-helical fold, these positions are often occupied by residues which do not conform to the pentapeptide consensus sequence. This suggests that the right-handed quadrilateral β-helix would exhibit plasticity to surface mutations.

The manor in which Np0276 is appended to the Np0275 does not deform the pentapeptide right-handed β-helix. This is most likely because:

Np0275 has no C-terminal cap

Np0276 has no N-terminal cap

The intervening genomic sequence between the two genes follows the pentapeptide repeat consensus sequence.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of detecting a DNA-interacting protein, the method comprising
   (a) contacting a protein with a purified *Mycobacterium tuberculosis* MfpA pentapeptide repeat protein (MtMfpA) which has had an assayable label bound thereto, wherein the label is a visible label, a fluorescent protein, a fluorescent organic compound less than 2000 molecular weight, a radioactive molecule, or an oligohistidine sequence, under conditions permitting the MtMfpA pentapeptide repeat protein to bind to a DNA-interacting protein, and
   (b) detecting the visible label, fluorescent protein, fluorescent organic compound less than 2000 molecular weight, radioactive molecule, or oligohistidine sequence, respectively, of the labeled MtMfpA that is bound to the DNA-interacting protein, so as to thereby detect the DNA-interacting protein.

2. The method of claim 1, wherein the assayable label is a fluorescent protein or a fluorescent organic compound of less than 2000 molecular weight.

3. The method of claim 1, wherein the DNA-interacting protein is a DNA metabolizing or DNA catabolizing enzyme.

4. The method of claim 3, wherein the DNA-metabolizing or DNA catabolizing enzyme is a DNA gyrase, a DNA polymerase, an RNA polymerase, a reverse transcriptase, a DNA ligase, an RNA ligase, a polynucleotide kinase, an alkaline phosphatase, a pyrophosphatase, a DNA glycosylase, a topoisomerase, a nicking enzyme, a restriction endonuclease, a ribonuclease, a recombinase, a deoxyribonuclease, or an exonuclease.

5. The method of claim 3, wherein the DNA-metabolizing or DNA catabolizing enzyme is a DNA gyrase.

6. The method of claim 1, wherein the DNA-interacting protein is a DNA-binding protein.

7. The method of claim 6, wherein the DNA-binding protein is a single stranded DNA binding protein, a transcription factor, a repressor, an activator, an enhancer, a helix-turn-helix protein, a zinc finger protein, a leucine zipper protein, a helix-loop-helix protein, a steroid receptor, or a homeodomain protein.

8. The method of claim 1, wherein the purified *Mycobacterium tuberculosis* MfpA is encoded by an Rv3361c gene.

9. The method of claim 1, wherein the purified *Mycobacterium tuberculosis* MfpA is 184 amino acids in length.

* * * * *

SEQUENCE LISTING

```
<160> NUMBER OF SEQ ID NOS: 7

<210> SEQ ID NO 1
<211> LENGTH: 180
<212> TYPE: PRT
<213> ORGANISM: Mycobacterium tuberculosis

<400> SEQUENCE: 1

Gln Gln Trp Val Asp Cys Glu Phe Thr Gly Arg Asp Phe Arg Asp Glu
1               5                   10                  15

Asp Leu Ser Arg Leu His Thr Glu Arg Ala Met Phe Ser Glu Cys Asp
            20                  25                  30

Phe Ser Gly Val Asn Leu Ala Glu Ser Gln His Arg Gly Ser Ala Phe
        35                  40                  45

Arg Asn Cys Thr Phe Glu Arg Thr Thr Leu Trp His Ser Thr Phe Ala
    50                  55                  60

Gln Cys Ser Met Leu Gly Ser Val Phe Val Ala Cys Arg Leu Arg Pro
65                  70                  75                  80

Leu Thr Leu Asp Asp Val Asp Phe Thr Leu Ala Val Leu Gly Gly Asn
                85                  90                  95

Asp Leu Arg Gly Leu Asn Leu Thr Gly Cys Arg Leu Arg Glu Thr Ser
            100                 105                 110

Leu Val Asp Thr Asp Leu Arg Lys Cys Val Leu Arg Gly Ala Asp Leu
        115                 120                 125

Ser Gly Ala Arg Thr Thr Gly Ala Arg Leu Asp Asp Ala Asp Leu Arg
    130                 135                 140

Gly Ala Thr Val Asp Pro Val Leu Trp Arg Thr Ala Ser Leu Val Gly
145                 150                 155                 160

Ala Arg Val Asp Val Asp Gln Ala Val Ala Phe Ala Ala Ala His Gly
                165                 170                 175

Leu Cys Leu Ala
            180

<210> SEQ ID NO 2
<211> LENGTH: 98
<212> TYPE: PRT
<213> ORGANISM: Nostoc punctiforme

<400> SEQUENCE: 2

Met Asp Val Glu Lys Leu Arg Gln Leu Tyr Ala Ala Gly Glu Arg Asp
1               5                   10                  15

Phe Ser Ile Val Asp Leu Arg Gly Ala Val Leu Glu Asn Ile Asn Leu
            20                  25                  30

Ser Gly Ala Ile Leu His Gly Ala Met Leu Asp Glu Ala Asn Leu Gln
        35                  40                  45

Gln Ala Asn Leu Ser Arg Ala Asp Leu Ser Gly Ala Thr Leu Asn Gly
    50                  55                  60

Ala Asp Leu Arg Gly Ala Asn Leu Ser Lys Ala Asp Leu Ser Asp Ala
65                  70                  75                  80

Ile Leu Asp Asn Ala Ile Leu Glu Gly Ala Ile Leu Asp Glu Ala Asn
                85                  90                  95
```

Leu Asn

<210> SEQ ID NO 3
<211> LENGTH: 181
<212> TYPE: PRT
<213> ORGANISM: Nostoc punctiforme
<220> FEATURE:
<221> NAME/KEY: misc_feature
<222> LOCATION: (99)..(99)
<223> OTHER INFORMATION: Xaa can be any naturally occurring amino acid

<400> SEQUENCE: 3

```
Met Asp Val Glu Lys Leu Arg Gln Leu Tyr Ala Ala Gly Glu Arg Asp
1               5                   10                  15

Phe Ser Ile Val Asp Leu Arg Gly Ala Val Leu Glu Asn Ile Asn Leu
            20                  25                  30

Ser Gly Ala Ile Leu His Gly Ala Met Leu Asp Glu Ala Asn Leu Gln
        35                  40                  45

Gln Ala Asn Leu Ser Arg Ala Asp Leu Ser Gly Ala Thr Leu Asn Gly
    50                  55                  60

Ala Asp Leu Arg Gly Ala Asn Leu Ser Lys Ala Asp Leu Ser Asp Ala
65                  70                  75                  80

Ile Leu Asp Asn Ala Ile Leu Glu Gly Ala Ile Leu Asp Glu Ala Val
                85                  90                  95

Leu Asn Xaa Ala Asn Leu Lys Ala Ala Asn Leu Glu Gln Ala Ile Leu
            100                 105                 110

Ser His Ala Asn Ile Arg Glu Ala Asp Leu Ser Glu Ala Asn Leu Glu
        115                 120                 125

Ala Ala Asp Leu Ser Gly Ala Asp Leu Ala Ile Ala Asp Leu Ser Glu
    130                 135                 140

Ala Asn Leu His Gln Ala Ala Leu Glu Arg Ala Asn Leu Thr Gly Ala
145                 150                 155                 160

Asn Leu Glu Asp Ala Asn Leu Glu Gly Thr Ile Leu Glu Gly Gly Asn
                165                 170                 175

Asn Asn Leu Ala Thr
            180
```

<210> SEQ ID NO 4
<211> LENGTH: 32
<212> TYPE: DNA
<213> ORGANISM: Nostoc punctiforme

<400> SEQUENCE: 4
atcccgctca tatggacgta gaaaaactca gg                              32

<210> SEQ ID NO 5
<211> LENGTH: 35
<212> TYPE: DNA
<213> ORGANISM: Nostoc punctiforme

<400> SEQUENCE: 5
atcccgctaa gcttctaatt taaaacggct tcatc                           35

<210> SEQ ID NO 6
<211> LENGTH: 5
<212> TYPE: PRT
<213> ORGANISM: Anabena sp.

-continued

```
<400> SEQUENCE: 6

Ala Asp Leu Ser Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Chemically synthesized pentapeptide
<220> FEATURE:
<221> NAME/KEY: MISC_FEATURE
<222> LOCATION: (1)..(1)
<223> OTHER INFORMATION: x = hydrophobic residue or uncharged polar
      residue
<220> FEATURE:
<221> NAME/KEY: MISC_FEATURE
<222> LOCATION: (2)..(2)
<223> OTHER INFORMATION: x= any amino acid
<220> FEATURE:
<221> NAME/KEY: MISC_FEATURE
<222> LOCATION: (3)..(3)
<223> OTHER INFORMATION: x = hydrophobic residue or uncharged polar
      residue
<220> FEATURE:
<221> NAME/KEY: MISC_FEATURE
<222> LOCATION: (4)..(5)
<223> OTHER INFORMATION: x= any amino acid

<400> SEQUENCE: 7

Xaa Xaa Xaa Xaa Xaa
1               5
```